United States Patent
Stevenson et al.

(10) Patent No.: US 8,889,088 B2
(45) Date of Patent: Nov. 18, 2014

(54) INTEGRATED PLANT FOR PRODUCING 2-ETHYL-HEXANOL AND METHACRYLIC ACID

(75) Inventors: Scott A. Stevenson, Houston, TX (US); Wugeng Liang, Katy, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 330 days.

(21) Appl. No.: 12/686,772

(22) Filed: Jan. 13, 2010

(65) Prior Publication Data

US 2010/0260647 A1  Oct. 14, 2010

Related U.S. Application Data

(62) Division of application No. 11/189,124, filed on Jul. 25, 2005, now Pat. No. 7,649,112.

(51) Int. Cl.
| | |
|---|---|
| *B01J 8/00* | (2006.01) |
| *B01J 19/00* | (2006.01) |
| *C07C 29/141* | (2006.01) |
| *C07C 51/235* | (2006.01) |
| *C07C 67/08* | (2006.01) |

(52) U.S. Cl.
CPC ............. *C07C 29/141* (2013.01); *C07C 51/235* (2013.01); *C07C 67/08* (2013.01)
USPC ............ 422/630; 422/129; 422/131; 422/187

(58) Field of Classification Search
USPC .................................. 422/630, 129, 131, 187
See application file for complete search history.

(56) References Cited

U.S. PATENT DOCUMENTS

| | | | | |
|---|---|---|---|---|
| 2,852,563 | A | * | 9/1958 | Hagemeyer, Jr. et al. ..... 568/461 |
| 3,763,247 | A | * | 10/1973 | Asnieres et al. .............. 568/882 |
| 3,903,172 | A | * | 9/1975 | Mooney et al. ................ 568/492 |
| 3,907,712 | A | | 9/1975 | Ohara et al. ................... 502/243 |
| 3,928,462 | A | | 12/1975 | Shiraishi et al. .............. 568/480 |
| 3,929,899 | A | | 12/1975 | Grasselli et al. .............. 568/476 |
| 3,933,751 | A | | 1/1976 | Callahan et al. .............. 568/477 |
| 3,936,505 | A | | 2/1976 | Oda et al. ....................... 502/215 |
| 3,946,081 | A | | 3/1976 | Wedemeyer et al. ......... 568/470 |
| 3,954,856 | A | | 5/1976 | Kobayashi et al. ........... 562/538 |

(Continued)

FOREIGN PATENT DOCUMENTS

| | | | | |
|---|---|---|---|---|
| EP | 0 025 715 B1 | 3/1981 | ............. | C07C 27/14 |
| EP | 0 169 449 B1 | 1/1986 | ............. | C07C 47/22 |

(Continued)

OTHER PUBLICATIONS

English Abstract of Japanese Patent No. 07149684; Date of Publication Jun. 13, 1995; 1 page.

(Continued)

*Primary Examiner* — Walter D Griffin
*Assistant Examiner* — Huy-Tram Nguyen
(74) *Attorney, Agent, or Firm* — Cantor Colburn LLP

(57) ABSTRACT

An integrated facility is disclosed for simultaneous production of butanal and methacrylic acid products where the facility utilizes a mixed methacrolein and isobutanal stream to make methacrylic acid. The facility is also designed to utilize downstream n-butanal products such as n-butanol and/or 2-ethyl-hexanol to make butyl-methacrylates and 2-ethylhexyl-methacrylate. A method is also disclosed which integrates the production of butanal derived products and methacrylic acid derived products.

26 Claims, 3 Drawing Sheets

(56) References Cited

U.S. PATENT DOCUMENTS

| | | | |
|---|---|---|---|
| 3,956,181 A | 5/1976 | Grasselli et al. | 502/212 |
| 3,956,378 A | 5/1976 | Grasselli et al. | 562/546 |
| 3,959,384 A | 5/1976 | Takenaka et al. | 568/479 |
| 3,963,645 A | 6/1976 | Gelbein | 502/248 |
| 3,966,823 A | 6/1976 | Takenaka et al. | 568/479 |
| 3,972,920 A | 8/1976 | Ishii et al. | 562/538 |
| 3,980,709 A | 9/1976 | Kubo et al. | 568/479 |
| 3,984,477 A | 10/1976 | Kubo et al. | 568/479 |
| 3,993,673 A | 11/1976 | McMullen | 549/531 |
| 4,001,317 A | 1/1977 | Grasselli et al. | 562/546 |
| 4,012,449 A | 3/1977 | Shikakura et al. | 568/471 |
| 4,025,565 A | 5/1977 | Oda et al. | 568/477 |
| 4,034,008 A | 7/1977 | Kutz et al. | 562/546 |
| 4,035,418 A | 7/1977 | Okada et al. | 562/538 |
| 4,040,978 A | 8/1977 | Li | 502/212 |
| 4,045,478 A | 8/1977 | Umemurs et al. | 562/535 |
| 4,049,577 A | 9/1977 | Childress et al. | 502/178 |
| 4,052,450 A | 10/1977 | Krabetz et al. | 562/546 |
| 4,052,462 A | 10/1977 | Sakakibara et al. | 568/477 |
| 4,060,545 A | 11/1977 | Miller et al. | 560/208 |
| 4,065,507 A | 12/1977 | Hardman et al. | 568/477 |
| 4,066,704 A | 1/1978 | Harris et al. | 568/475 |
| 4,075,244 A * | 2/1978 | Akiyama et al. | 562/535 |
| 4,078,004 A | 3/1978 | Schlaefer et al. | 568/479 |
| 4,087,382 A | 5/1978 | Khoobiar | 502/249 |
| 4,111,984 A | 9/1978 | Ishii et al. | 562/538 |
| 4,111,985 A | 9/1978 | Okada et al. | 562/546 |
| 4,118,419 A | 10/1978 | Ishii et al. | 562/534 |
| 4,124,634 A | 11/1978 | Gotoh et al. | 562/532 |
| 4,127,603 A | 11/1978 | Bljumberg et al. | 562/533 |
| 4,129,600 A | 12/1978 | Childress et al. | 568/479 |
| 4,134,859 A | 1/1979 | Kurtz et al. | 502/249 |
| 4,148,757 A | 4/1979 | Brazdil et al. | 502/205 |
| 4,151,117 A | 4/1979 | Schlaefer | 502/212 |
| 4,155,938 A | 5/1979 | Yamamoto et al. | 568/479 |
| 4,162,234 A | 7/1979 | Grasselli et al. | 502/205 |
| 4,166,808 A | 9/1979 | Daumas et al. | 502/249 |
| 4,170,570 A | 10/1979 | Zagata et al. | 502/211 |
| 4,171,328 A | 10/1979 | Umemura et al. | 568/479 |
| 4,171,454 A | 10/1979 | Miller et al. | 562/546 |
| 4,174,354 A | 11/1979 | Grasselli et al. | 585/626 |
| 4,174,459 A | 11/1979 | Sakamoto et al. | 562/534 |
| 4,176,234 A | 11/1979 | Grasselli et al. | 562/546 |
| 4,180,678 A | 12/1979 | Wada et al. | 562/534 |
| 4,182,907 A | 1/1980 | Grasselli et al. | 562/546 |
| 4,184,981 A | 1/1980 | Vanderspurt | 502/209 |
| 4,186,152 A | 1/1980 | Yamamoto et al. | 568/477 |
| 4,190,608 A | 2/1980 | Grasselli et al. | 562/546 |
| 4,195,187 A | 3/1980 | Vanderspurt | 562/545 |
| 4,205,181 A | 5/1980 | Murib | 560/214 |
| 4,208,303 A | 6/1980 | Sasaki et al. | 502/38 |
| 4,209,640 A | 6/1980 | Yamamoto et al. | 562/532 |
| 4,212,767 A | 7/1980 | Daniel | 502/211 |
| 4,217,309 A | 8/1980 | Umemura et al. | 568/477 |
| 4,219,670 A | 8/1980 | Okada et al. | 562/546 |
| 4,224,187 A | 9/1980 | Vanderspurt | 502/212 |
| 4,224,193 A | 9/1980 | Vanderspurt | 502/307 |
| 4,225,466 A | 9/1980 | Wada et al. | 502/209 |
| 4,230,639 A | 10/1980 | Khoobiar | 568/471 |
| 4,230,640 A | 10/1980 | Khoobiar | 568/477 |
| 4,240,931 A | 12/1980 | Milberger et al. | 502/306 |
| 4,245,118 A | 1/1981 | Yamamoto et al. | 562/532 |
| 4,248,803 A | 2/1981 | Vanderspurt | 568/477 |
| 4,250,339 A | 2/1981 | Sakamoto et al. | 568/471 |
| 4,252,683 A | 2/1981 | Khoobiar | 502/211 |
| RE30,545 E | 3/1981 | Khoobiar | 502/249 |
| 4,258,217 A | 3/1981 | Aoshima et al. | 568/474 |
| 4,261,858 A | 4/1981 | Khoobiar | 502/211 |
| 4,267,385 A | 5/1981 | Umemura et al. | 568/479 |
| 4,267,386 A | 5/1981 | Vanderspurt | 568/480 |
| 4,271,040 A | 6/1981 | Khoobiar | 502/211 |
| 4,272,408 A | 6/1981 | Daniel | 502/211 |
| 4,272,637 A | 6/1981 | Yamamoto et al. | 568/780 |
| 4,276,196 A | 6/1981 | Dalton et al. | 502/212 |
| 4,280,928 A | 7/1981 | Kirch et al. | 502/205 |
| 4,280,929 A | 7/1981 | Shaw et al. | 502/215 |
| 4,292,203 A | 9/1981 | Milberger et al. | 502/304 |
| 4,297,247 A | 10/1981 | Krabetz et al. | 502/310 |
| 4,298,763 A | 11/1981 | Engelbach et al. | 568/479 |
| 4,303,550 A | 12/1981 | Callahan et al. | 502/24 |
| 4,306,088 A | 12/1981 | Nakamura et al. | 568/471 |
| 4,306,090 A | 12/1981 | Kirch et al. | 568/481 |
| 4,311,611 A | 1/1982 | Sasaki et al. | 502/22 |
| 4,316,856 A | 2/1982 | Guttmann et al. | 558/322 |
| 4,320,227 A | 3/1982 | Matsumoto et al. | 562/534 |
| 4,321,160 A | 3/1982 | Farrington et al. | 502/209 |
| 4,323,703 A | 4/1982 | Grasselli et al. | 562/546 |
| 4,332,971 A | 6/1982 | Dalton et al. | 568/480 |
| 4,337,364 A | 6/1982 | Solomon | 568/475 |
| 4,338,462 A * | 7/1982 | Wheaton | 562/533 |
| 4,339,355 A | 7/1982 | Decker et al. | 502/343 |
| 4,339,608 A | 7/1982 | Pretzer et al. | |
| 4,341,900 A | 7/1982 | Ishii et al. | 562/532 |
| 4,351,963 A | 9/1982 | Ray et al. | 568/477 |
| 4,354,044 A | 10/1982 | Aoshima et al. | 568/479 |
| 4,356,316 A | 10/1982 | Aoshima et al. | 560/208 |
| RE31,088 E | 11/1982 | Grasselli et al. | 562/535 |
| 4,370,490 A | 1/1983 | Gruber et al. | 560/214 |
| 4,374,759 A | 2/1983 | Khoobiar | 502/249 |
| 4,377,501 A | 3/1983 | Khoobiar | 502/211 |
| 4,380,664 A | 4/1983 | Ishii et al. | 562/546 |
| 4,388,223 A | 6/1983 | Ferlazzo et al. | 502/211 |
| 4,388,225 A | 6/1983 | Solomon | 502/346 |
| 4,397,771 A | 8/1983 | Grasselli et al. | 502/306 |
| 4,404,397 A | 9/1983 | Daniel | 562/546 |
| 4,413,147 A | 11/1983 | Khoobiar | 568/476 |
| 4,414,134 A | 11/1983 | Friedrich et al. | 502/204 |
| 4,415,482 A | 11/1983 | Ebner | 502/205 |
| 4,419,270 A | 12/1983 | Ueshima et al. | 502/209 |
| 4,424,141 A | 1/1984 | Grasselli et al. | 502/205 |
| 4,425,255 A | 1/1984 | Toyoda et al. | 502/38 |
| 4,426,542 A * | 1/1984 | Barker et al. | 568/883 |
| 4,442,308 A | 4/1984 | Arntz et al. | 568/480 |
| 4,443,555 A | 4/1984 | Callahan et al. | 502/211 |
| 4,443,556 A | 4/1984 | Aoki et al. | 502/212 |
| 4,444,906 A | 4/1984 | Callahan et al. | 502/211 |
| 4,444,907 A | 4/1984 | Ohdan et al. | 502/211 |
| 4,446,328 A | 5/1984 | Aoshima et al. | 568/479 |
| 4,453,006 A | 6/1984 | Shaw et al. | 562/545 |
| 4,454,346 A | 6/1984 | Khoobiar | 562/535 |
| 4,467,113 A | 8/1984 | Matsumoto et al. | 562/535 |
| 4,471,061 A | 9/1984 | Shaw et al. | 502/34 |
| 4,471,062 A | 9/1984 | Farrington et al. | 502/34 |
| 4,479,013 A | 10/1984 | Khoobiar | 568/479 |
| 4,489,170 A | 12/1984 | Krabetz et al. | 502/211 |
| 4,499,301 A | 2/1985 | Murib | 562/546 |
| 4,503,247 A | 3/1985 | Khoobiar | 562/535 |
| 4,511,671 A | 4/1985 | Saito et al. | 502/242 |
| 4,518,523 A | 5/1985 | Blum et al. | 502/209 |
| 4,528,398 A | 7/1985 | Callahan et al. | 562/534 |
| 4,530,916 A | 7/1985 | Matsumoto et al. | 502/209 |
| 4,532,365 A | 7/1985 | Khoobiar | 568/479 |
| 4,535,188 A | 8/1985 | Khoobiar | |
| 4,537,874 A | 8/1985 | Sato et al. | 502/311 |
| 4,537,998 A | 8/1985 | Shum et al. | 568/483 |
| 4,547,588 A | 10/1985 | Khoobiar | 562/535 |
| 4,552,860 A | 11/1985 | Murib | 502/242 |
| 4,556,731 A | 12/1985 | Guttmann et al. | 562/546 |
| 4,558,028 A | 12/1985 | Tsuneki et al. | 502/211 |
| 4,558,029 A | 12/1985 | Paparizos et al. | 502/211 |
| 4,558,154 A | 12/1985 | Shum et al. | 562/537 |
| RE32,082 E | 2/1986 | Khoobiar | 568/476 |
| 4,585,883 A | 4/1986 | Briggs | 556/42 |
| 4,596,784 A | 6/1986 | Kennelly et al. | 502/209 |
| 4,598,162 A * | 7/1986 | Forster et al. | 568/448 |
| 4,621,155 A | 11/1986 | Ueshima et al. | 562/534 |
| 4,652,673 A | 3/1987 | Matsumoto et al. | 562/535 |
| 4,677,084 A | 6/1987 | Bergna | 502/8 |
| 4,684,750 A * | 8/1987 | Kessen et al. | 568/883 |
| 4,698,440 A * | 10/1987 | Blair et al. | 560/205 |
| 4,720,575 A | 1/1988 | Gruber | 560/214 |
| 4,732,884 A | 3/1988 | Sarumaru et al. | 502/205 |
| 4,778,930 A | 10/1988 | Grasselli et al. | 568/477 |
| 4,803,190 A | 2/1989 | Sarumaru et al. | 502/205 |

(56) References Cited

U.S. PATENT DOCUMENTS

| | | | |
|---|---|---|---|
| 4,816,603 A | 3/1989 | Oh-Kita et al. | 562/538 |
| 4,839,417 A * | 6/1989 | Suetterlin et al. | 524/833 |
| 4,855,275 A | 8/1989 | Suresh et al. | 502/353 |
| 4,871,700 A | 10/1989 | Uchida et al. | 502/51 |
| 4,916,103 A | 4/1990 | Martan et al. | 592/212 |
| 4,925,823 A | 5/1990 | Krabetz et al. | 502/211 |
| 4,925,981 A | 5/1990 | Shimizu et al. | |
| 4,946,819 A | 8/1990 | Sasaki et al. | 502/214 |
| 4,954,650 A | 9/1990 | Abe et al. | 562/534 |
| 4,956,493 A | 9/1990 | Ueoka et al. | |
| 4,962,133 A | 10/1990 | Chromecek et al. | |
| 4,968,846 A | 11/1990 | Kuragano et al. | 568/479 |
| 4,985,592 A | 1/1991 | Ishii et al. | 562/534 |
| 5,017,542 A | 5/1991 | Martan et al. | 502/209 |
| 5,059,573 A | 10/1991 | Sasaki et al. | 502/205 |
| 5,072,052 A | 12/1991 | Boeck et al. | 568/479 |
| 5,081,314 A | 1/1992 | Kissel et al. | 568/479 |
| 5,082,819 A | 1/1992 | Boeck et al. | 502/212 |
| 5,087,744 A | 2/1992 | Krabetz et al. | |
| 5,094,990 A | 3/1992 | Sasaki et al. | 502/214 |
| 5,102,847 A | 4/1992 | Yamamoto et al. | 502/209 |
| 5,132,269 A | 7/1992 | Sasaki et al. | 502/205 |
| 5,138,100 A | 8/1992 | Matsuura | 568/474 |
| 5,139,988 A | 8/1992 | Sasaki et al. | 502/206 |
| 5,144,090 A | 9/1992 | Honda et al. | 568/476 |
| 5,153,162 A | 10/1992 | Kurimoto et al. | 502/209 |
| 5,155,262 A | 10/1992 | Etzkorn et al. | 562/534 |
| 5,166,119 A | 11/1992 | Oh-Kita et al. | 502/205 |
| 5,173,468 A | 12/1992 | Boehning et al. | 502/209 |
| 5,183,936 A | 2/1993 | Etzkorn et al. | 562/532 |
| 5,198,578 A | 3/1993 | Etzkorn et al. | 562/532 |
| 5,198,581 A | 3/1993 | Kawajiri et al. | 562/546 |
| 5,206,431 A | 4/1993 | Hashiba et al. | 562/534 |
| 5,208,371 A | 5/1993 | Kuroda et al. | 562/538 |
| 5,218,146 A | 6/1993 | Takata et al. | 562/535 |
| 5,221,653 A | 6/1993 | Jaeger et al. | 502/159 |
| 5,221,767 A | 6/1993 | Boehning et al. | 562/532 |
| 5,225,389 A | 7/1993 | Caillod et al. | 502/205 |
| 5,245,083 A | 9/1993 | Matsuura | 568/479 |
| 5,248,819 A * | 9/1993 | Matsumoto et al. | 562/532 |
| 5,250,485 A | 10/1993 | Kuroda et al. | 502/159 |
| 5,264,627 A * | 11/1993 | Tazaki et al. | 562/599 |
| 5,276,178 A | 1/1994 | Onodera et al. | 562/537 |
| 5,300,707 A | 4/1994 | Caillod et al. | 568/480 |
| 5,349,092 A | 9/1994 | Watanabe et al. | 568/480 |
| 5,364,825 A | 11/1994 | Neumann et al. | 502/311 |
| 5,380,933 A | 1/1995 | Ushikubo et al. | 562/549 |
| 5,491,258 A | 2/1996 | Watanabe et al. | 562/538 |
| 5,532,199 A | 7/1996 | Watanabe et al. | 502/311 |
| 5,602,280 A | 2/1997 | Nagai et al. | 562/532 |
| 5,618,974 A | 4/1997 | Kurimoto et al. | 562/532 |
| 5,670,702 A | 9/1997 | Jackson et al. | 560/208 |
| 5,681,790 A | 10/1997 | Kim et al. | 502/164 |
| 5,684,188 A | 11/1997 | Hefner et al. | 562/532 |
| 5,700,752 A | 12/1997 | Kurimoto et al. | 502/311 |
| 5,728,894 A | 3/1998 | Nagano et al. | 568/479 |
| 5,739,391 A | 4/1998 | Ruppel et al. | 562/532 |
| 5,817,865 A | 10/1998 | Machhammer et al. | 560/208 |
| 5,821,390 A | 10/1998 | Ruppel et al. | 568/470 |
| 5,827,939 A * | 10/1998 | Paumard | 560/205 |
| 5,856,259 A | 1/1999 | Watanabe et al. | 502/305 |
| 5,865,957 A * | 2/1999 | Ueda et al. | 203/25 |
| 5,877,108 A | 3/1999 | Suresh et al. | 502/20 |
| 5,892,108 A | 4/1999 | Shiotani et al. | 562/532 |
| 5,929,275 A | 7/1999 | Wada et al. | 562/546 |
| 5,948,683 A | 9/1999 | Koermer et al. | 436/37 |
| 5,981,804 A | 11/1999 | Kurimoto et al. | 568/479 |
| 5,990,348 A | 11/1999 | Lyon et al. | 562/549 |
| 6,028,220 A | 2/2000 | Wada et al. | 562/546 |
| 6,043,184 A | 3/2000 | Karmakar et al. | 502/208 |
| 6,060,419 A | 5/2000 | Wijesekera et al. | |
| 6,069,271 A | 5/2000 | Tanimoto et al. | 562/545 |
| 6,100,432 A | 8/2000 | Borgel et al. | |
| 6,171,571 B1 | 1/2001 | Bedard et al. | 423/594.7 |
| 6,172,267 B1 * | 1/2001 | Urata et al. | 568/454 |
| 6,211,414 B1 | 4/2001 | Bogdanovic et al. | |
| 6,492,564 B1 | 12/2002 | Wiese et al. | |
| 6,610,881 B1 * | 8/2003 | Riedel et al. | 562/35 |
| 6,864,391 B2 | 3/2005 | Krokoszinski | |
| 2001/0044558 A1 * | 11/2001 | Kelly | 568/459 |
| 2002/0188151 A1 * | 12/2002 | Inoue et al. | 560/205 |
| 2003/0069327 A1 | 4/2003 | Walz et al. | |
| 2003/0233014 A1 * | 12/2003 | Chun et al. | 562/535 |
| 2004/0015011 A1 | 1/2004 | Krokoszinski et al. | |
| 2004/0158009 A1 * | 8/2004 | Mays et al. | 526/89 |
| 2004/0213711 A1 * | 10/2004 | Ha et al. | 422/198 |
| 2004/0236049 A1 * | 11/2004 | Fuchs et al. | 526/317.1 |
| 2005/0209469 A1 | 9/2005 | Shutt et al. | |

FOREIGN PATENT DOCUMENTS

| | | | |
|---|---|---|---|
| EP | 0 223 877 B1 | 6/1987 | B01J 23/88 |
| EP | 0 267 556 B1 | 5/1988 | B01J 23/88 |
| EP | 0 279 374 B1 | 8/1988 | B01J 23/88 |
| EP | 0 450 596 B1 | 10/1991 | B01J 23/88 |
| EP | 0486291 A1 | 11/1991 | |
| EP | 0 460 932 B1 | 12/1991 | B01J 23/88 |
| EP | 0 501 794 B1 | 9/1992 | B01J 23/887 |
| EP | 0 523 727 B1 | 1/1993 | B01J 23/88 |
| EP | 0 558 028 B1 | 9/1993 | B01J 23/88 |
| EP | 0 563 025 A1 | 9/1993 | B01J 23/881 |
| EP | 0 574 895 A1 | 12/1993 | B01J 23/88 |
| EP | 0 630 879 A1 | 12/1994 | B01J 23/887 |
| EP | 0 685 260 A2 | 12/1995 | B01J 23/887 |
| EP | 0 767 161 A1 | 4/1997 | C07C 45/35 |
| EP | 1857477 A1 | 1/2006 | |
| JP | 07149684 | 6/1995 | |
| JP | 07196571 | 8/1995 | |
| JP | 07267636 A | 10/1995 | |
| JP | 1135510 | 2/1999 | |
| JP | 1180066 | 3/1999 | |
| JP | 11-226412 A | 8/1999 | |
| JP | 20003242974 | 12/2000 | |
| WO | WO 91/08185 | 6/1991 | B01J 8/06 |
| WO | WO-00/64913 A1 * | 11/2000 | C07C 309/00 |
| WO | WO-02/079269 A1 * | 10/2002 | C08F 2/00 |
| WO | 2005063672 A1 | 7/2005 | |

OTHER PUBLICATIONS

English Abstract of Japanese Patent No. 07196571 A; Date of Publication Aug. 1, 1995; 2 pages.

English Abstract of Japanese Patent No. 07267636 A; Date of Publication Oct. 17, 1995; 2 pages.

English Abstract of Japanese Patent No. 1135510; Date of Publication Feb. 9, 1999; 1 page.

English Abstract of Japenese Patent No. 1180066; Date of Publication Mar. 23, 1999; 1 page.

English Abstract of Japanese Patent No. 2000342974 A; Date of Publication Dec. 12, 2000; 2 pages.

European Search Report of the European Patent Office; European Patent Application No. 06 774 687.5-1454; Filing Date Aug. 20, 2013; 9 pages.

International Search Report and Written Opinion of the International Searching Authority Application No. PCT/US06/28817; International Filing Date: Jul. 25, 2006; Date of mailing: Sep. 21, 2007; 9 pages.

Japanese Patent No. 11226412; Date of Publication: Aug. 24, 1999; Abstract Only, 1 page.

* cited by examiner

INTEGRATED PLANT FOR PRODUCING 2-ETHYL-HEXANOL AND METHACRYLIC ACID

RELATED APPLICATIONS

This application is a divisional application of U.S. patent application Ser. No. 11/189,124, filed 25 Jul. 2005 (Jul. 25, 2005), now U.S. Pat. No. 7,649,112, issued 19 Jan. 2010 (Jan. 19, 2010).

BACKGROUND OF THE INVENTION

1. Field of the Invention

The present invention relates to a process and a system for integrating the manufacturing of 2-ethyl-hexanol and methacrylic acid.

More particularly, the present invention relates to a process and a system for integrating the manufacturing of 2-ethyl-hexanol and its derivatives and methacrylic acid and its derivatives, where the process includes converting a methacrolein precursor stream in the presence of an oxygen containing gas and a mixed oxide catalyst into a methacrolein-containing stream, concurrently hydroformylating a propylene stream in the presence of a mixture of carbon monoxide and hydrogen and a hydroformylation catalyst into a butanals stream, separating the butanals stream into an n-butanal stream and an isobutanal stream, combining the methacrolein-containing stream and the isobutanal or isobutyraldehyde stream and converting the combined stream in the presence of an oxygen containing gas and a heteropolyacid catalyst to a methacrylic acid-containing stream. The present invention also relates to the production of n-butanal derived products, methacrylic acid derived products and products derived from both n-butanal and methacrylic acid.

2. Description of the Related Art

Currently, processes exist for the conversion of propylene into butanals and isobutene into methacrylic acid. As a by-product of the propylene conversion process, an undesired by-product is produced, isobutanal or isobutyraldehyde. This waste product is generally either burned for fuel value or disposed of.

Thus, there is a need in the art for a process that can readily utilize this waste stream in a value enhancing process to make a more valuable product and to reduce or eliminate the need for disposal of an unwanted by-product or waste stream.

DEFINITIONS AND ABBREVIATIONS

The term IBA means isobutanal sometimes also referred to as isobutyraldehyde.

The term MAC means methacrolein.

The term MAA means methacrylic acid.

The term T means temperature.

The term P means pressure.

The term HC means hydrocarbon.

The term aldehyde feedstock means a stream including a mixture of isobutanal and methacrolein.

The term GC means gas chromatography.

The term FID means flame ionization detector of a GC.

The term h or hr or hrs means hours.

The term g means grams.

The term mL means milliliter.

The term min or min. means minutes.

The term wt % or wt. % means weight percent.

The term vol % or vol. % means volume percent.

The term DI means deionized water.

SUMMARY OF THE INVENTION

The present invention provides an integrated system for making butanals and/or unsaturated acid derived products, where the system includes a butanals production and utilization subsystem and an unsaturated acid production and utilization subsystem. The butanals production and utilization subsystem includes a supply of propylene and a supply of a mixture of carbon monoxide and hydrogen (syn gas), a hydroformylation reactor component, an aldehyde separation component having an n-butanal output and an isobutanal output, and an n-butanal conversion component. The hydroformylation reactor component is adapted to convert propylene and syn gas in the presence of a hydroformylation catalyst into butanals comprising n-butanal and isobutanal. The aldehyde separation component is adapted to separate the butanals into n-butanal and isobutanal. The n-butanal conversion component is adapted to convert the n-butanal into n-butanal-derived products. The methacrylic acid production and utilization subsystem includes a supply of a methacrolein precursor such as isobutene, t-butyl-alcohol, or the like, a supply of an oxidizing agent, a first oxidation reactor component, a second oxidation reactor component, and a methacrylic acid conversion component. The first oxidation reactor component is adapted to convert the methacrolein precursor and the oxidizing agent into methacrolein in the presence of a mixed oxide oxidation catalyst. The second oxidation reactor component is adapted to simultaneously convert the methacrolein, the isobutanal and the oxidizing agent into methacrylic acid in the presence of a heteropolyacid catalyst. The methacrylic acid conversion component is adapted to convert the methacrylic acid into methacrylic acid-derived products which may also involve the use of butanal products.

The present invention provides an integrated system for making butanals and/or unsaturated acid derived products, where the system includes a butanals production and utilization subsystem and an unsaturated acid production and utilization subsystem. The butanals production and utilization subsystem includes a supply of propylene and a supply of a mixture of carbon monoxide and hydrogen (syn gas), a hydroformylation reactor component, an aldehyde separation component having a n-butanal output and an isobutanal output, a primary n-butanal conversion component and optionally a secondary n-butanal conversion component. The hydroformylation reactor component converts propylene and syn gas into butanals comprising n-butanal and isobutanal in the presence of a hydroformylation catalyst. The aldehyde separation component is adapted to separate the butanals into n-butanal and isobutanal. The primary n-butanal conversion component is adapted to convert the separated n-butanal into primary n-butanal-derived products and the secondary n-butanal conversion component is adapted to convert primary n-butanal-derived products into secondary n-butanal-derived products. The methacrylic acid production and utilization subsystem includes a supply of a methacrolein precursor, a supply of an oxidizing agent, a first oxidation reactor component, a second oxidation reactor component, a primary methacrylic acid conversion component and optionally a secondary methacrylic acid conversion component. The first oxidation reactor component is adapted to convert the methacrolein precursor and the oxidizing agent into methacrolein in the presence a mixed oxide oxidation catalyst. The second oxidation reactor component is adapted to simultaneously convert the methacrolein, the isobutanal and the oxidizing agent into methacrylic acid in the presence of a heteropolyacid catalyst. The primary methacrylic acid conversion component is adapted to convert the methacrylic acid into primary methacrylic acid-derived products. The secondary methacrylic acid conversion component is adapted to convert primary methacrylic acid derived products into secondary methacrylic acid derived products.

The present invention also provides an integrated system for making alcohols and unsaturated acids and esters, where the plant includes an alcohol production subsystem and an unsaturated acid/ester subsystem. The alcohol production subsystem includes a supply of propylene and a supply of a mixture of carbon monoxide and hydrogen (syn gas), a hydroformylation reactor component, an aldehyde separation component having a n-butanal output and an isobutanal output, a n-butanol production component, a poly-n-butanal production component and a 2-ethyl-hexanol component. The hydroformylation reactor component is adapted to convert propylene and syn gas into n-butanal and isobutanal in the presence of a hydroformylation catalyst. The aldehyde separation component is adapted to separate n-butanal and isobutanal. The butanol production component, the polybutanal production component, and the 2-ethyl-hexanol component are adapted to produce n-butanol, n-butanal polymers, and 2-ethyl-hexanol. The unsaturated acids and esters subsystem includes a supply of a methacrolein precursor, a supply of an oxidizing agent, a first oxidation reactor component, a second oxidation reactor component, and a methyl-methacrylate production component having a supply of methanol. The first oxidation reactor component is adapted to convert the methacrolein precursor and the oxidizing agent into methacrolein in the presence of a mixed oxide oxidation catalyst. The second oxidation reactor component is adapted to simultaneously convert the methacrolein, the isobutanal and the oxidizing agent into methacrylic acid in the presence of a heteropolyacid catalyst. The methyl-methacrylate production component is adapted to convert methacrylic acid and methanol into methyl-methacrylate in the presence of an esterification catalyst. The integrated system can also include a butyl-methacrylate production component and a 2-ethyl-hexyl-methacrylate component, where the butyl-methacrylate component is adapted to convert methacrylic acid and n-butanol into butyl-methacrylate in the presence of an esterification catalyst and the 2-ethyl-hexyl-methacrylate component is adapted to convert methacrylic acid and 2-ethyl-hexanol into 2-ethyl-hexyl-methacrylate in the presence of an esterification catalyst. The integrated system can also include components to make butyl-methacrylate copolymers and/or 2-ethyl-hexyl-methacrylate copolymers.

The present invention provides a method for integrating a butanals production and utilization facility and a methacrylic acid production and utilization facility, where the method includes the step of contacting propylene and a syn gas with a hydroformylation catalyst to form a hydroformylation product including n-butanal (also known as n-butyraldehye), and isobutanal (also known as isobutyraldehyde). The hydroformylation product is then separated into an n-butanal product and a isobutanal product. The n-butanal product can then be polymerized to form n-butanal polymers, hydrogenated to n-butanol product, and/or dimerized and hydrogenated into 2-ethyl-hexanol product. Simultaneously or non-simultaneously with the hydroformylation step, a methacrolein precursor and an oxidizing agent are contacted with a mixed metal oxidation catalyst to form a methacrolein product. The methacrolein product and the isobutanal product are then contacted with a heteropolyacid catalyst to form a methacrylic acid product. The method can also include the step of contacting methanol and methacrylic acid product in the presence of an esterification catalyst to form methyl-methacrylate. The method can also include the step of reacting the n-butanol product and the methacrylic acid product in the presence of an esterification catalyst to form n-butyl-methacrylate. The method can also include the step of contacting the 2-ethyl-hexanol product and the methacrylic acid product in the presence of an esterification catalyst to form 2-ethyl-hexyl-methacrylate. The method can also include the step of polymerizing methacrylic acid into polymethacryclic acid, polymerizing methyl-methacrylate into poly-methyl-methacrylate, polymerizing n-butyl-methacrylate to poly-n-butyl-methacrylate, or polymerizing 2-ethyl-hexyl-methacrylate to poly-2-ethyl-hexyl-methacrylate.

The present invention provides a method for integrating a butanals production and utilization facility and a methacrylic acid production and utilization facility, where the method includes the step of hydroformylating a propene (propylene) containing stream with a syn gas stream in the presence of a hydroformylation catalyst to produce a hydroformylation product stream including n-butanal (-butyraldehye) and isobutanal (isobutyraldehyde). The hydroformylation product stream is then separated into an n-butanal containing stream and an isobutanal containing stream. The n-butanal containing stream can then be polymerized to an poly-n-butanal containing product stream. Simultaneously or non-simultaneously with the hydroformylation and separation steps, a methacrolein precursor containing stream is oxidized in the presence of an oxidizing agent containing stream and a mixed metal oxidation catalyst to form a methacrolein containing stream. The methacrolein containing stream and the isobutanal containing stream are then co-oxidized in the presence of a second oxidizing agent containing stream and a heteropolyacid catalyst to form a methacrylic acid containing stream. The method can also include the step esterifying a methacrylic acid containing stream with a methanol containing stream in the presence of an esterification catalyst to produce a methyl-methacrylate containing stream. The method can also include the steps of hydrogenating an n-butanal containing stream to form a n-butanol containing stream and reacting the n-butanol containing stream with a methacrylic acid containing stream to from a n-butyl-methacrylate containing stream. The method can also include the steps of dimerizing an n-butanal containing stream in the presence of a dimerization catalyst to form a dimerized product stream and hydrogenating the dimerized product stream in the presence of a hydrogenation catalyst to form a 2-ethyl-hexanol containing stream and esterifying a methacrylic acid containing stream with the 2-ethyl-hexanol containing stream in the presence of an esterification catalyst to form 2-ethyl-hexyl-methacrylate. The method can also include the step of polymerizing methacrylic acid into poly-methacrylic acid, polymerizing butyl-methacrylate into poly-butyl-methacrylate, polymerizing 2-ethyl-hexyl-methacrylate into poly-2-ethyl-hexyl-methacrylate or polymerizing mixtures of these and other methacrylates into acrylate co-polymers, ter-polymers, etc.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
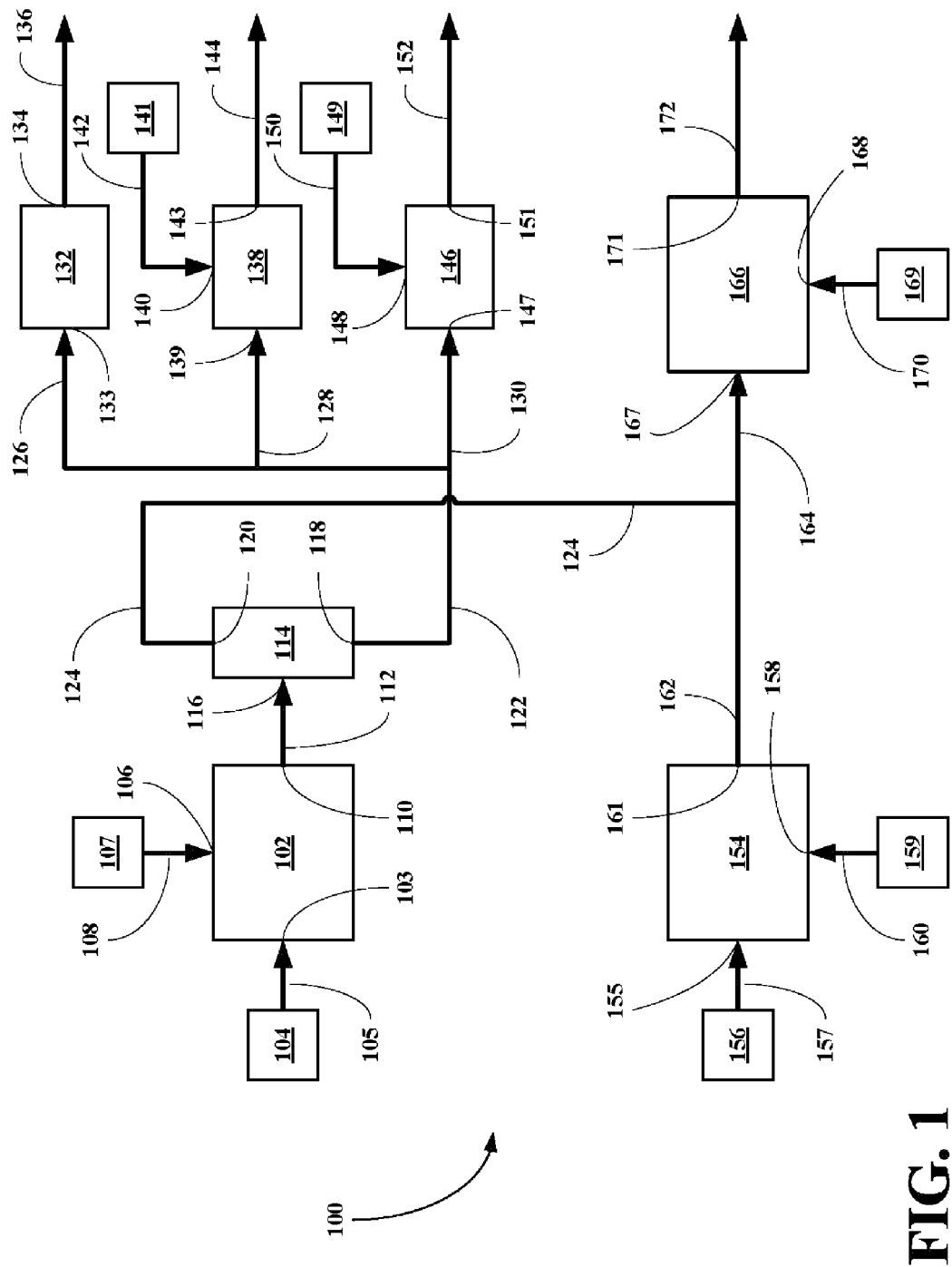
FIG. 1 depicts a preferred embodiment of an integrated butanal/methacrylic acid facility of this invention.

The inventors have found that a chemical plant can be constructed that integrates a methacrylic acid production and utilization facility with a butanals production and utilization facility. The integration of the two facilities reduces by-product waste, more efficiently utilizes output streams for the co-production of final products having starting materials derived from the two facilities independently or collectively and provides for better utilization of by-product streams.

The present invention broadly relates to an integrated production facility for making butanal and methacrylic acid derived products, where the facility includes a butanal production and utilization system and a methacrylic acid production and utilization system. The butanal production and utilization system includes a supply of propylene and a supply of a syn gas, a hydroformylation reactor component, and an aldehyde separation component having an n-butanal output and an isobutanal output. The hydroformylation reactor component is adapted to convert propylene into n-butanal and isobutanal in the presence of syn gas and a hydroformylation catalyst. The aldehyde separation component separates n-butanal and isobutanal. The methacrylic acid production and utilization system includes a supply of a methacrolein precursor, a methacrolein precursor oxidation reactor component, and a methacrylic acid formation reactor component. The methacrolein precursor oxidation reactor component is adapted to convert the methacrolein precursor into methacrolein in the presence of an oxidizing agent and a mixed oxide oxidation catalyst. The methacrylic acid formation reactor is adapted to convert a mixture of methacrolein and isobutanal simultaneously into methacrylic acid in the presence of an oxidizing agent and a heteropolyacid catalyst. The integrated production facility can also include a butanol production unit, a polybutanal production unit, a 2-ethyl-hexanol unit, a methyl-methacrylate production unit, a butyl-methacrylate production unit and/or a 2-ethyl-hexyl-methacrylate unit. The integrated production facility can also include a poly-methyl-methacrylate production unit, a poly-methacrylic acid production unit, a poly-butyl-acrylate production unit, a poly-2-ethyl-hexyl-methacrylate production unit and/or units for making acrylate co-polymers, ter-polymers, etc.

The present invention provides a method for co-producing butanal and methacrylic acid products, where the method includes the steps of converting propylene to butanals in the presence of a syn gas and a hydroformylation catalyst adapted, where the butanals include n-butanal (n-butyraldehye) and isobutanal (isobutyraldehyde). The butanals are then separated into n-butanal and isobutanal. The n-butanal can then be polymerized to form polymer including n-butanal as a monomer, hydrogenated to form n-butanol and/or dimerized and hydrogenated to form 2-ethyl-hexanol. Simultaneously or not with the butanal producing steps, a methacrolein precursor is oxidized in the presence of an oxidizing agent and a mixed metal oxidation catalyst to form methacrolein. The methacrolein and the isobutanal are then oxidized simultaneously in the presence of an oxidizing agent and a heteropolyacid catalyst to form methacrylic acid. The method can also include the step reacting methanol and methacrylic acid in the presence of an esterification catalyst to form methyl-methacrylate. The method can also include the step of reacting butanol and methacrylic acid in the presence of an esterification catalyst to form butyl-methacrylate. The method can also include the step of reacting the 2-ethyl-hexanol and methacrylic acid in the presence of an esterification catalyst to form 2-ethyl-hexyl-methacrylate. The method can also include the step of polymerizing methacrylic acid in the presence or absence of a polymerization catalyst into poly-methacrylic acid. The method can also include the step of polymerizing methyl-methacrylate in the presence or absence of a polymerization catalyst into poly-methyl-methacrylate. The method can also include the step of polymerizing butyl-methacrylate in the presence or absence of a polymerization catalyst into poly-butyl-methacrylate. The method can also include the step of polymerizing 2-ethyl-hexyl-methacrylate in the presence or absence of a polymerization catalyst into poly-2-ethyl-hexyl-methacrylate. The method can also include the steps of polymerizing a mixture of acrylates in the presence or absence of a polymerization catalyst into polymer including two or more acrylate monomers.

SUITABLE CATALYST, MATERIALS AND COMPONENTS

Suitable Facility Components

Reactor components include reactors and all associated equipment for operating the reactors such as fixed bed reactors, moving bed reactors, fluid bed reactors, stirred tank reactors, plug flow reactors, distillation column reactors, and other reactors for carrying out gas phase, liquid phase or mixed phase reaction, where the reactors can also include piping, feed lines, recycle lines, compressors, expanders, heaters, cooling jackets, temperature controllers, pressures controllers, valves, computer control units, operator control units, etc.

Separation components includes decanters, distillation columns, extraction columns, extractive distillation columns, catalytic distillations columns, or other devices for separating components and also include piping, feed lines, recycle lines, compressors, expanders, heaters, cooling jackets, temperature controllers, pressures controllers, valves, computer control units, operator control units, etc.

Facilities or systems include all reactor components, separation components, hydrogenation components, polymerization components, dimerization components, purification components, etc., each can also include piping, feed lines, recycle lines, compressors, expanders, heaters, cooling jackets, temperature controllers, pressures controllers, valves, computer control units, operator control units, etc.

Suitable Reagents

Suitable esterification catalysts include, without limitation, acids and bases, both Lewis and Brønsted. Exemplary examples of such catalyst include sulfuric acid, phosphoric acid, hydrochloric acid, acid ion exchange resins, sodium hydroxide, base ion exchange resins, etc.

Suitable dimerization catalysts include, without limitation, sodium hydroxide, potassium hydroxide, or the like.

Suitable hydrogenation catalysts include, without limitation, hydrogenation catalysts including a transition metal including a group 8, 9, 10, and 11 (Fe, Ru, Os, Co, Rh, Ir, Ni, Pd, Pt, Cu, Ag, Au) elements from the IUPAC Table of Elements. The hydrogenation catalysts can be homogeneous or heterogeneous, support or supported.

Suitable methacrolein precursors include, without limitation, isobutylene, t-butanol, or other similar materials that can be oxidized to methacrolein.

Suitable mixed metal oxide catalysts include, without limitation, any mixed metal oxide catalyst capable of oxidizing a methacrolein precursor to methacrolein especially molybdenum based mixed metal oxide patents, exemplary examples of such catalyst are described in U.S. Pat. Nos. 3,907,712; 3,928,462; 3,929,899; 3,933,751; 3,936,505; 3,956,378; 4,012,449; 4,025,565; 4,035,418; 4,111,984; 4,170,570; 4,171,454; 4,190,608; 4,224,193; 4,240,931; 4,250,339; 4,252,683; 4,258,217; 4,261,858; 4,267,385; 4,267,386; 4,271,040; 4,272,408; 4,292,203; 4,306,088; 4,306,090; 4,332,971; 4,339,355; 4,354,044; 4,377,501; 4,380,664;

4,404,397; 4,413,147; 4,414,134; 4,424,141; 4,446,328; 4,454,346; 4,489,170; 4,503,247; 4,511,671; 4,535,188; 4,537,874; 4,547,588; 4,556,731; 4,558,029; 4,596,784; 4,732,884; 4,778,930; 4,803,190; 4,816,603; 4,871,700; 4,916,103; 4,925,823; 4,946,819; 4,954,650; 5,059,573; 5,072,052; 5,081,314; 5,082,819; 5,094,990; 5,102,847; 5,132,269; 5,138,100; 5,144,090; 5,155,262; 5,166,119; 5,183,936; 5,198,578; 5,221,653; 5,225,389; 5,245,083; 5,250,485; 5,264,627; 5,276,178; 5,300,707; 5,349,092; 5,364,825; 5,380,933; 5,491,258; 5,532,199; 5,602,280; 5,670,702; 5,684,188; 5,728,894; 5,739,391; 5,817,865; 5,821,390; 5,856,259; 6,028,220; 6,069,271; 6,171,571; or RE32,082, incorporated herein by reference.

Suitable aldehyde conversion catalysts include, without limitation, any catalyst that will simultaneously oxidize mixtures of methacrolein and isobutanal to methacrylic acid. Preferred aldehyde conversion catalysts include, without limitation, heteropolyacid catalysts. Preferred heteropolyacid catalysts include the heteropolyacid catalysts disclosed in co-filed and co-pending U.S. patent application Ser. No. associated with Express Mail Label No. ER 411-451601 US. These catalysts have the general formula:

$$Mo_{12}P_aV_bCu_cMI_dMII_eMIII_fO_g \quad (I)$$

where:
  MI is selected from the group consisting of bismuth (Bi), boron (B) and mixtures or combinations thereof,
  MII is selected from the group consisting of potassium (K), rubidium (Rb), cesium (Cs), thallium (Tl), and mixtures or combinations thereof,
  MIII is selected from the group consisting of antimony (Sb), cerium (Ce), niobium (Nb), indium (In), iron (Fe), chromium (Cr), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof,
  a is a number having a value between about 0.1 and about 3.5,
  b is a number having a value between about 0.01 and about 5.0,
  c is a number having a value between about 0.0 and about 1.5,
  d is a number having a value between about 0.01 and about 2.0 when MI is Bi, or a value between about 0.01 and about 5.0 when MI is B and when d represent a mixture of Bi and B, then the Bi ranges between about 0.01 and about 2.0 and B ranges between about 0.01 and about 5.0,
  e is a number having a value between about 0.0 and about 5.0,
  f is a number having a value between about 0.0 and about 5.0, and
  g is a number having a value representing a sufficient number of oxygen atoms to balance the oxidation state of the catalyst of formula (I).

Other preferred catalysts include catalysts described in United States and Foreign patents that include examples of both methacrolein and isobutanal oxidation which are included in the following list of U.S. Pat. Nos. 3,840,595; 3,865,873; 3,875,220; 3,925,464; 3,856,182; 3,965,163; 3,998,876; 3,998,877; 4,000,088; 4,001,316; 4,017,423; 4,042,533; 4,042,625; 4,051,179; 4,052,450; 4,052,450; 4,070,397; 4,101,448; 4,115,441; 4,118,419; 4,124,634; 4,124,634; 4,138,366; 4,138,366; 4,165,296; 4,166,190; 4,169,070; 4,172,051; 4,180,678; 4,212,767; 4,212,767; 4,212,767; 4,223,161; 4,225,466; 4,238,359; 4,240,930; 4,250,054; 4,252,681; 4,252,682; 4,252,683; 4,259,211; 4,261,858; 4,261,859; 4,261,860; 4,271,040; 4,272,408; 4,273,676; 4,297,247; 4,301,030; 4,301,031; 4,305,843; 4,314,074; 4,319,042; 4,320,227; 4,339,355; 4,341,900; 4,347,163; 4,356,114; 4,356,316; 4,358,608; 4,358,610; 4,404,397; 4,440,948; 4,443,555; 4,444,906; 4,467,113; 4,469,810; 4,471,062; 4,489,170; 4,528,398; 4,530,916; 4,558,028; 4,558,029; 4,565,801; 4,595,778; 4,745,217; 4,803,302; 4,804,778; 4,814,305; 4,891,347; 4,925,823; 4,925,980; 4,954,650; 4,968,838; 4,985,592; 4,985,592; 5,102,846; 5,102,847; 5,198,579; 4,621,155; 4,652,673; 4,720,575; 4,757,038; 4,816,603; 4,966,990; 5,093,521; 5,104,844; 5,126,307; 5,153,162; 5,173,468; 5,206,431; 5,221,767; 5,239,115; 5,264,627; 5,420,091 5,422,326; or 5,521,137, and European Pat. Nos. EP0113156 B1; EP0064371 B1; EP0265733 B1; EP0180997 B1; or EP0268201 B1, all of which are incorporated herein by reference.

DETAILED DESCRIPTION OF THE DRAWINGS

Referring now to FIG. 1, a preferred embodiment of a facility of this invention, generally 100, is shown to include a hydroformylation system 102 having to a propylene input 103 connected to a propylene source 104 supporting a propylene feed stream 105 to the hydroformylation system 102 and a syn gas input 106 connected to a syn gas source 107 supporting a syn gas feed stream 108 to the hydroformylation system 102. The hydroformylation system 102 also includes a hydroformylation output 110. The hydroformylation system 102 is adapted to convert the propylene and syn gas (a mixture of carbon monoxide and hydrogen) in the presence of a hydroformylation catalyst, preferably a cobalt carbonyl based hydroformylation catalyst, into a hydroformylation product stream 112 comprising a mixture of n-butanal and isobutanal which exits through the output 110. The stream 112 also includes small amounts of n-butanol and isobutanol.

The hydroformylation product stream 112 is then forwarded to a distillation system 114. The separation system 114 includes a hydroformylation product stream input 116, an n-butanal output 118 and an isobutanal output 120. The distillation system 114 separates the hydroformylation product stream 112 into an n-butanal-containing stream 122 and an isobutanal-containing stream 124. The n-butanal-containing stream 122 can then be split into three substreams 126, 128, and 130, depending on the n-butanal products desired.

If n-butanal polymerization products are desired, then the substream 126 exists and is forwarded to a polymerization unit 132 including an n-butanal input 133 and a polymerization product output 134, where the n-butanal is polymerized alone or in combination with other monomers to form a polymer product stream 136, where the polymer product includes n-butanal monomer units.

If n-butanol is desired, then the n-butanal substream 128 exists and is forwarded to a hydrogenation unit 138 including an n-butanal input 139, a reducing agent input 140 connected to a reducing agent source 141 supporting a reducing agent feed stream 142 and an n-butanol output 143. In the hydrogenation unit 138, the n-butanal is hydrogenated to n-butanol in the presence of the reducing agent, preferably hydrogen, and a hydrogenation catalyst to form an n-butanol stream 144.

If 2-ethyl-hexanol is desired, then the n-butanal substream 130 exists and is forwarded to a dimerization unit 146 including an n-butanal input 147, a reducing agent input 148 connected to a reducing agent source 149 supporting a reducing agent feed stream 150 and a 2-ethyl-hexanol output 151. In the dimerization unit 146, the n-butanal is dimerized in the presence of a dimerization catalyst, preferably sodium hydroxide, and then hydrogenated in the presence of a reducing agent, preferably hydrogen, and a second hydrogenation catalyst, preferably a Raney Nickel catalyst, to form a 2-ethyl-hexanol stream 152.

The facility 100 also includes, in parallel, a first oxidation reactor system 154 including a methacrolein precursor input 155 connected to a methacrolein precursor source 156 supporting a methacrolein precursor stream 157 and an oxidizing agent input 158 connected to a source of an oxidizing agent 159 supporting an oxidizing agent stream 160. The reactor system 154 also includes a methacrolein output 161 through which a methacrolein-containing stream 162 exits. The first oxidation reactor system 154 can be operated simultaneously or not with the hydroformylation system 102.

The methacrolein-containing stream 162 is then combined with the isobutanal-containing stream 124 to form a combined stream 164, which is then forwarded to a second oxidation reactor system 166 through a combined stream input 167. Of course, the two streams 124 and 162 can also be independently fed to the second reactor system 166. The second reactor system 166 includes an oxidizing agent input 168 connected to a source of an oxidizing agent 169 supporting an oxidizing agent stream 170. The reactor system 166 also includes a methacrylic acid output 171 through which a methacrylic acid-containing stream 172 exits.

Figure 2:
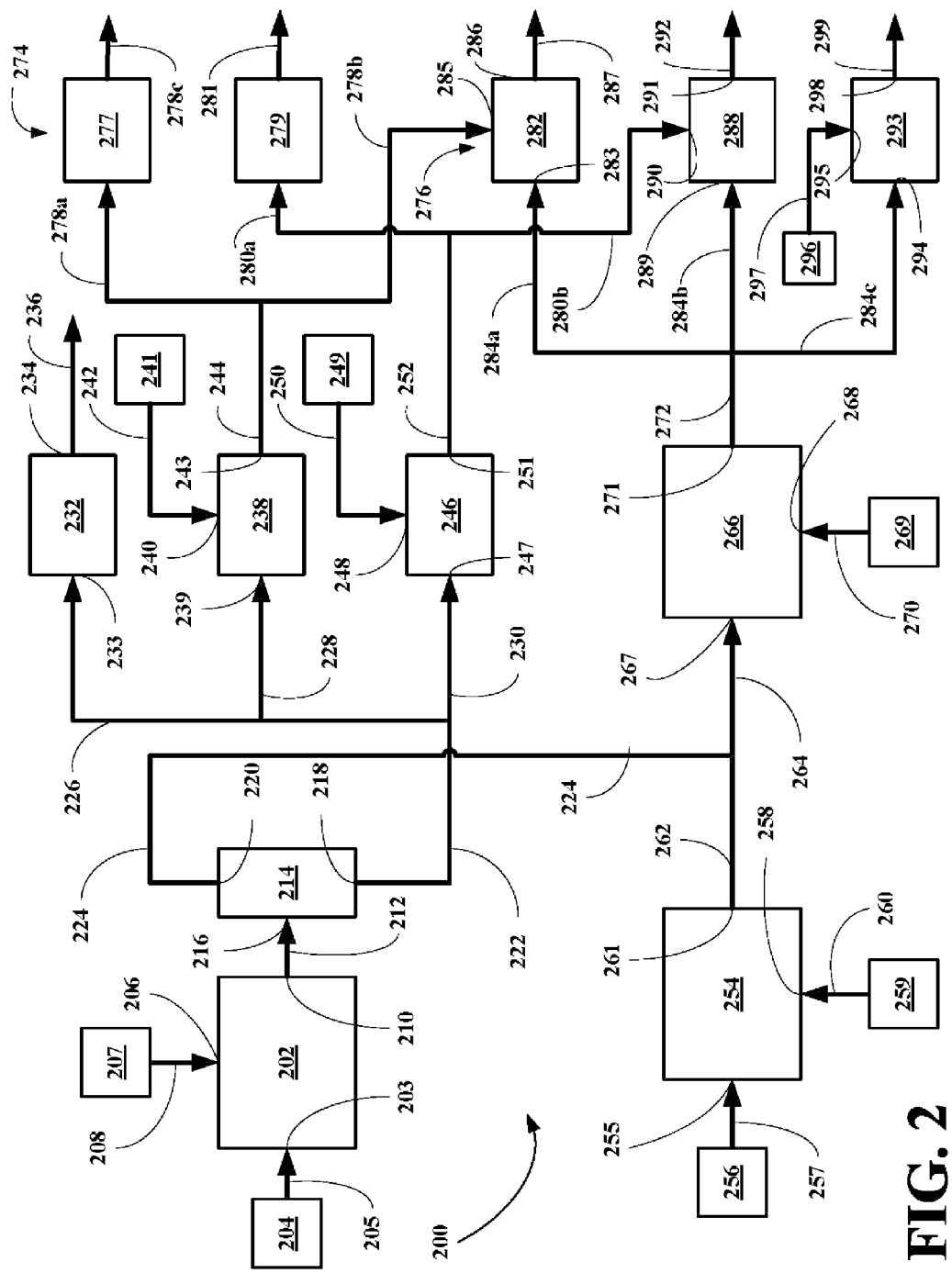
FIG. 2 depicts another preferred embodiment of an integrated butanal/methacrylic acid facility of this invention.

Referring now to FIG. 2, another preferred embodiment of a facility of this invention, generally 200, is shown to include a hydroformylation system 202 having a propylene input 203 connected to a propylene source 204 supporting a propylene feed stream 205 to the hydroformylation system 202 and a syn gas input 206 connected to a syn gas source 207 supporting a syn gas feed stream 208 to the hydroformylation system 202. The hydroformylation system 202 also includes a hydroformylation output 210. The hydroformylation system 202 is adapted to convert the propylene and syn gas (a mixture of carbon monoxide and hydrogen) in the presence of a hydroformylation catalyst, preferably a cobalt carbonyl based hydroformylation catalyst, into a hydroformylation product stream 212 comprising a mixture of n-butanal and isobutanal which exits through the output 210. The stream 212 also includes small amounts of n-butanol and isobutanol.

The hydroformylation product stream 212 is then forwarded to a distillation system 214. The distillation system 214 includes a hydroformylation product stream input 216, an n-butanal output 218 and an isobutanal output 220. The distillation system 214 separates the hydroformylation product stream 212 into an n-butanal-containing stream 222 and an isobutanal-containing stream 224. The n-butanal-containing stream 222 can then be split into three substreams 226, 228, and 230, depending on the n-butanal products desired.

If n-butanal polymerization products are desired, then the substream 226 exists and is forwarded to a polymerization unit 232 including an n-butanal input 233 and a polymerization product output 234, where the n-butanal is polymerized alone or in combination with other monomers to form a polymer product stream 236, where the polymer product includes n-butanal monomer units.

If n-butanol is desired, then the n-butanal substream 228 exists and is forwarded to a hydrogenation unit 238 including an n-butanal input 239, a reducing agent input 240 connected to a reducing agent source 241 supporting a reducing agent feed stream 242 and an n-butanol output 243. In the hydrogenation unit 238, the n-butanal is hydrogenated to n-butanol in the presence of the reducing agent, preferably hydrogen, and a hydrogenation catalyst to form an n-butanol stream 244.

If 2-ethyl-hexanol is desired, then the n-butanal substream 230 exists and is forwarded to a dimerization unit 246 including an n-butanal input 247, a reducing agent input 248 connected to a reducing agent source 249 supporting a reducing agent feed stream 250 and a 2-ethyl-hexanol output 251. In the dimerization unit 246, the n-butanal is dimerized in the presence of a dimerization catalyst, preferably sodium hydroxide, and then hydrogenated in the presence of a reducing agent, preferably hydrogen, and a second hydrogenation catalyst, preferably a Raney Nickel catalyst, to form a 2-ethyl-hexanol stream 252.

The facility 200 also includes, in parallel, a first oxidation reactor system 254 including a methacrolein precursor input 255 connected to a methacrolein precursor source 256 supporting a methacrolein precursor stream 257 and an oxidizing agent input 258 connected to a source of an oxidizing agent 259 supporting an oxidizing agent stream 260. The reactor system 254 also includes a methacrolein output 261 through which a methacrolein-containing stream 262 exits. The first oxidation reactor system 254 can be operated simultaneously or not with the hydroformylation system 202.

The methacrolein-containing stream 262 is then combined with the isobutanal-containing stream 224 to form a combined stream 264, which is then forwarded to a second oxidation reactor system 266 through a combined stream input 267. Of course, the two stream 224 and 262 can also be independently fed to the second reactor system 266. The second reactor system 266 includes an oxidizing agent input 268 connected to a source of an oxidizing agent 269 supporting an oxidizing agent stream 270. The reactor system 266 also includes a methacrylic acid output 271 through which a methacrylic acid-containing stream 272 exits.

The facility 200 can also include a secondary n-butanal conversion system 274 and a primary methacrylic acid conversion system 276. The secondary n-butanal conversion system 274 can include an n-butanol conversion unit 277 to form an output product stream 278c from an n-butanol substream 278a, which can be a butyl acetate unit, a butyl acrylate unit or other units that convert n-butanol into an output product. The second n-butanal conversion system 274 can also include a 2-ethyl-hexanol conversion unit 279 to form another output product stream 281 from a 2-ethyl-hexanol substream 280a, which can include a di-iso-octyl-phthalate unit, a 2-ethyl-hexyl cellulose unit, or other units that convert 2-ethyl-hexanol into an output product.

The primary methacrylic acid conversion system 276 can include an n-butyl-methacrylate production unit 282 including a methacrylic acid input 283 for receiving a methacrylic acid stream 284a derived from the methacrylic acid stream 272. The n-butyl-methacrylate production unit 282 also includes an n-butanol input 285 supporting an n-butanol substream 278b and an n-butyl-methacrylate output 286 through which an n-butyl-methacrylate stream 287 exits the n-butyl-methacrylate production unit 282.

The primary methacrylic acid conversion system 276 can include a 2-ethyl-hexyl-methacrylate production unit 288 including a methacrylic acid input 289 for receiving a methacrylic acid stream 284b derived from the methacrylic acid stream 272. The 2-ethyl-hexyl-methacrylate production unit 288 also includes 2-ethyl-hexanol input 290 supporting a 2-ethyl-hexanol substream 280b and a 2-ethyl-hexyl-methacrylate output 291 through which a 2-ethyl-hexyl-methacrylate stream 292 exits the 2-ethyl-hexyl-methacrylate production unit 288.

The primary methacrylic acid conversion system 276 can include a methyl-methacrylate production unit 293 including a methacrylic acid input 294 for receiving a methacrylic acid stream 284c derived from the methacrylic acid stream 272. The methyl-methacrylate production unit 293 also includes methanol input 295 connected to a methanol source 296 supporting a methanol stream 297 and a methyl-methacrylate output 298 through which a methyl-methacrylate stream 299 exits the methyl-methacrylate production unit 293.

Figure 3:
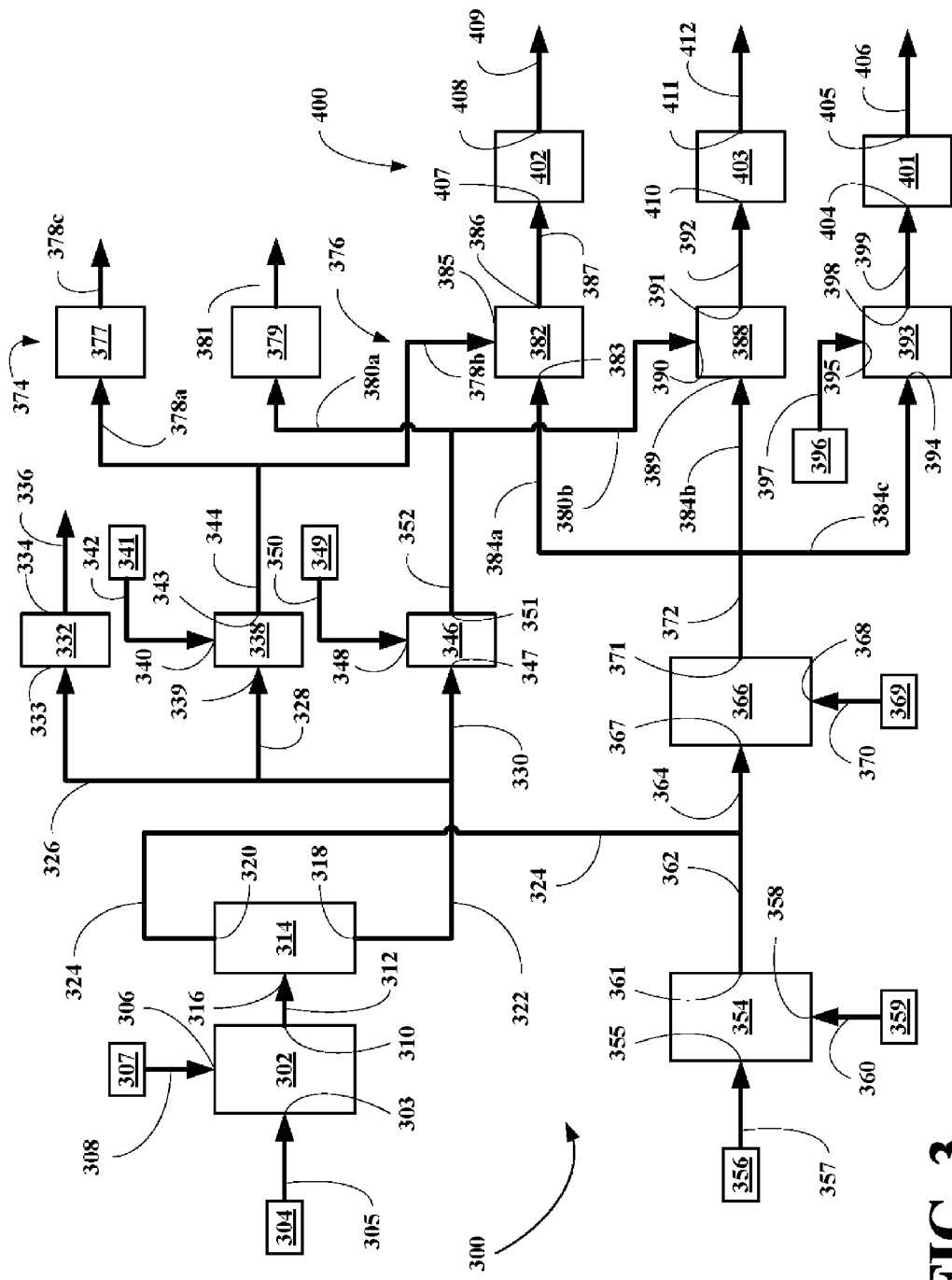
FIG. 3 depicts another preferred embodiment of an integrated butanal/methacrylic acid facility of this invention.

Referring now to FIG. 3, another preferred embodiment of a facility of this invention, generally 300, is shown to include a hydroformylation system 302 having a propylene input 303 connected to a propylene source 304 supporting a propylene feed stream 305 to the hydroformylation system 302 and a syn gas input 306 connected to a syn gas source 307 supporting a syn gas feed stream 308 to the hydroformylation system 302. The hydroformylation system 302 also includes a hydroformylation output 310. The hydroformylation system 302 is adapted to convert the propylene and syn gas (a mixture of carbon monoxide and hydrogen) in the presence of a hydroformylation catalyst, preferably a cobalt carbonyl based hydroformylation catalyst, into a hydroformylation product stream 312 comprising a mixture of n-butanal and isobutanal which exits through the output 310. The stream 312 also includes small amounts of n-butanol and isobutanol.

The hydroformylation product stream 312 is then forwarded to a distillation system 314. The distillation system 314 includes a hydroformylation product stream input 316, an n-butanal output 318 and an isobutanal output 320. The distillation system 314 separates the hydroformylation product stream 312 into an n-butanal-containing stream 322 and an isobutanal-containing stream 324. The n-butanal-containing stream 322 can then be split into three substreams 326, 328, and 330, depending on the n-butanal products desired.

If n-butanal polymerization products are desired, then the substream 326 exists and is forwarded to a polymerization unit 332 including an n-butanal input 333 and a polymerization product output 334, where the n-butanal is polymerized alone or in combination with other monomers to form a polymer product stream 336, where the polymer product includes n-butanal monomer units.

If n-butanol is desired, then the n-butanal substream 328 exists and is forwarded to a hydrogenation unit 338 including an n-butanal input 339, a reducing agent input 340 connected to a reducing agent source 341 supporting a reducing agent feed stream 342 and an n-butanol output 343. In the hydrogenation unit 338, the n-butanal is hydrogenated to n-butanol in the presence of the reducing agent, preferably hydrogen, and a hydrogenation catalyst to form an n-butanol stream 344.

If 2-ethyl-hexanol is desired, then the n-butanal substream 330 exists and is forwarded to a dimerization unit 346 including an n-butanal input 347, a reducing agent input 348 connected to a reducing agent source 349 supporting a reducing agent feed stream 350 and a 2-ethyl-hexanol output 351. In the dimerization unit 346, the n-butanal is dimerized in the presence of a dimerization catalyst, preferably sodium hydroxide, and then hydrogenated in the presence of the reducing agent, preferably hydrogen, and a second hydrogenation catalyst, preferably a Raney Nickel catalyst, to form a 2-ethyl-hexanol stream 352.

The facility 300 also includes, in parallel, a first oxidation reactor system 354 including a methacrolein precursor input 355 connected to a methacrolein precursor source 356 supporting a methacrolein precursor stream 357 and an oxidizing agent input 358 connected to a source of an oxidizing agent 359 supporting an oxidizing agent stream 360. The reactor system 354 also includes a methacrolein output 361 through which a methacrolein-containing stream 362 exits. The first oxidation reactor system 354 can be operated simultaneously or not with the hydroformylation system 302.

The methacrolein-containing stream 362 is then combined with the isobutanal-containing stream 324 to form a combined stream 364, which is then forwarded to a second oxidation reactor system 366 through a combined stream input 367. Of course, the two streams 324 and 362 can also be independently fed to the second reactor system 366. The second reactor system 366 includes an oxidizing agent input 368 connected to a source of an oxidizing agent 369 supporting an oxidizing agent stream 370. The reactor system 366 also includes a methacrylic acid output 371 through which a methacrylic acid-containing stream 372 exits.

The facility 300 can also include secondary n-butanal conversion system 374 and primary methacrylic acid conversion system 376. The secondary n-butanal conversion system 374 can include an n-butanol conversion unit 377 to form an output product stream 378c from an n-butanol substream 378a, which can be a butyl acetate unit, a butyl acrylate unit or other units that convert n-butanol into an output product. The second n-butanal conversion system 374 can also include a 2-ethyl-hexanol conversion unit 379 to form another output product stream 381 from a 2-ethyl-hexanol substream 380a, which can include a di-iso-octyl phthalate unit, a 2-ethylhexyl cellulose unit, or other units that convert 2-ethyl-hexanol into an output product.

The primary methacrylic acid conversion system 376 can include an n-butyl-methacrylate production unit 382 including a methacrylic acid input 383 for receiving a methacrylic acid stream 384a derived from the methacrylic acid stream 372. The n-butyl-methacrylate production unit 382 also includes an n-butanol input 385 supporting an n-butanol substream 378b and an n-butyl-methacrylate output 386 through which an n-butyl-methacrylate stream 387 exits the n-butyl-methacrylate production unit 382.

The primary methacrylic acid conversion system 376 can include a 2-ethyl-hexyl-methacrylate production unit 388 including a methacrylic acid input 389 for receiving a methacrylic acid stream 384b derived from the methacrylic acid stream 372. The 2-ethyl-hexyl-methacrylate production unit 388 also includes a 2-ethyl-hexanol input 390 supporting a 2-ethyl-hexanol substream 380b and a 2-ethyl-hexyl-methacrylate output 391 through which a 2-ethyl-hexyl-methacrylate stream 392 exits the 2-ethyl-hexyl-methacrylate production unit 388.

The primary methacrylic acid conversion system 376 can include a methyl-methacrylate production unit 393 including a methacrylic acid input 394 for receiving a methacrylic acid stream 384c derived from the methacrylic acid stream 372. The methyl-methacrylate production unit 393 also includes methanol input 395 connected to a methanol source 396 supporting a methanol stream 397 and a methyl-methacrylate output 398 through which a methyl-methacrylate stream 399 exits the methyl-methacrylate production unit 393.

The facility 300 can also include secondary methacrylic acid conversion system 400 including a poly-methyl-methacrylate unit 401, a poly-butyl-methacrylate unit 402, and a poly-2-ethyl-hexyl-methacrylate unit 403. The poly-methyl-methacrylate unit 401 includes a methyl-methacrylate input 404 for receiving the methyl-methacrylate stream 399 and a poly-methyl-methacrylate output 405 supporting an poly-methyl-methacrylate output stream 406. The poly-butyl-methacrylate unit 402 includes a butyl-methacrylate input 407 for receiving the butyl-methacrylate stream 387 and a poly-methyl-methacrylate output 408 supporting an poly-methyl-methacrylate output stream 409. The poly-2-ethyl-hexyl-methacrylate unit 403 includes a 2-ethyl-hexyl-methacrylate input 410 for receiving the 2-ethyl-hexyl-methacrylate stream 392 and a poly-2-ethyl-hexylmethacrylate output 411 supporting an poly-2-ethyl-hexyl-methacrylate output stream 412. The three polymerization units 401, 402 and 403 are adapted to polymerize the acrylate monomer in the presence of an acrylate polymerization catalyst. The catalyst used in polymerization can be any Ziegler-Natta type polymerization catalyst including traditional Ziegler-Natta type polymerization catalysts, metallocene polymerization catalysts, or newer Ziegler-Natta type polymerization catalysts. Exemplary, but non-limiting, examples include those disclosed in U.S. Pat. Nos. 6,683,146, 6,673,885, 6,610,801, 6,593,440, 6,300,440, 6,175,037, 6,111,041, 5,578,544, 5,491,244, 5,399,641, 5,359,018, 5,349,022, 4,912,183, 4,370,449, 4,203,867, 4,163,092, 4,151,147, 4,151,146, 4,071,508, 4,060,678, 4,058,491, and 4,036,788, incorporated herein by reference.

GENERAL REACTION CONDITIONS AND FEEDSTOCK COMPOSITIONS

Aldehyde Feedstock Conversion

The catalysts used in the process of the present invention can be used without a carrier, or can be supported on or diluted with an inert carrier. Suitable inert carriers include, without limitation, silicates, silicas, aluminates, aluminas, silica-aluminas, silicon carbide, zirconias, titanias, magnesia, similar oxides or mixtures or combinations thereof.

The catalysts of this invention are ideally suited for producing an unsaturated acid, preferably a conjugated unsaturated acid such as methacrylic acid by gas-phase catalytic oxidation of a vapor or vapor stream including an aldehyde feedstock comprising isobutanal and methacrolein at a temperature, at a pressure and for a time sufficient to convert the aldehydes in the aldehyde feedstock to methacrylic acid. The vapor stream used to contact the catalysts of the present invention generally includes a sufficient amount of aldehydes in the aldehyde feedstock that is converted into an output stream containing a commercial quantity of methacrylic acid. Preferably, the vapor or vapor stream includes from about 1 vol. % to about 20 vol. % of the aldehydes in the aldehyde feedstock, and particularly, the vapor or vapor stream includes from about 3 to about 10 vol. % of aldehydes in the aldehyde feedstock. Typically, an aldehyde feed for the preparation of methacrylic acid may also contain large amounts of water and smaller amounts of impurities such as carbon monoxide, carbon dioxide, acetone, acetic acid, acrolein, methacrylic acid, isobutylene and other saturated and unsaturated hydrocarbons, lower saturated aldehydes, etc., but such impurities have substantially no effect on the conversion of the aldehydes to unsaturated acids.

Although the gas-phase catalytic oxidation reaction of an aldehyde feed stock over a catalyst of this invention can be economically performed in the presence of air, one class of preferred oxidizing agents for use in this invention are oxygen-containing gases having a higher oxygen content than air. Another preferred oxidizing agent for use in this invention is pure oxygen. An amount of the oxidizing agent used in the conversion of the aldehyde feedstock to methacrylic acid is set relative to a molar ratio of oxygen to aldehydes in the aldehyde feedstock. Generally, the molar ratio has a value between about 0.3 and about 4.0, preferably, the ratio has a value between about 0.8 and about 3.0. The oxidizing gas may be diluted with or contain an inert gas such as nitrogen, steam, carbon dioxide, etc., recycled oxygen-containing gases or mixtures or combinations thereof.

In producing methacrylic acid using the catalysts of this invention, the oxidation is generally carried out at a reaction pressure between sub-ambient and several atmospheres above ambient, preferably, the pressure is near ambient or as low as practical. The oxidation reaction using the catalysts of this invention is generally carried out at an elevated temperature, preferably, at a temperature between about 230° C. and about 450° C., particularly, at a temperature between about 250° C. and about 400° C. and more particularly, at a temperature between about 250° C. and about 350° C. The oxidation reaction using the catalysts of this invention can be carried out using a variety of reactor systems including a fixed bed reactor (a reactor having one or more fixed catalyst beds or zones), a fluidized bed reactor (recycling catalyst in a gas entrained reaction environment), a moving bed reactor (catalyst moves in and out of the catalyst zone(s)), a continuous stirred tank reactor or any other reactor system geared for carrying out an oxidizing reaction such as the conversion of isobutyraldehyde to methacrylic acid.

Aldehyde Feedstocks

The system and method of this invention are designed to produce methacrylic acid from an aldehyde feedstock including a mixture of isobutanal derived from a 2-ethyl-hexanol production and utilization facility and methacrolein derived in a first stage oxidation reaction of a methacrylic acid production and utilization facility. Thus, the system and the method of this invention are designed to improve the overall efficiencies of stream utilization and improve downstream product manufacturing by having needed streams within the same facility. That is, methyl-methacrylate polymers and copolymers can be made on site as well as 2-ethyl-hexyl-methacrylate polymers and copolymer and butyl-methacrylate copolymers can be made on site.

The system of this invention and method based thereon are designed to use aldehyde feedstocks including a mixture of isobutanal from the butanal portion of the system and methacrolein from the methacrylic acid portion of the system and to convert the mixture to methacrylic acid in the presence of a heteropolyacid catalyst capable of simultaneously oxidizing the mixture to methacrylic acid. As is noted below, certain heteropolyacids are capable of simultaneously oxidizing the mixture, while others are not and the certain catalysts are preferred.

One preferred mixture of aldehydes has a composition ranging between about 5 wt. % isobutanal and about 95 wt. % methacrolein to about 95 wt. % isobutanal and about 5 wt. % methacrolein. Another preferred mixture of aldehydes has a composition ranging between about 10 wt. % isobutanal and about 90 wt. % methacrolein to about 90 wt. % isobutanal and about 10 wt. % methacrolein. Another preferred mixture of aldehydes has a composition ranging between about 15 wt. % isobutanal and about 85 wt. % methacrolein to about 85 wt. % isobutanal and about 15 wt. % methacrolein. Another preferred mixture of aldehydes has a composition ranging between about 20 wt. % isobutanal and about 80 wt. % methacrolein to about 80 wt. % isobutanal and about 20 wt. % methacrolein. Another preferred mixture of aldehydes has a composition ranging between about 25 wt. % isobutanal and about 75 wt. % methacrolein to about 75 wt. % isobutanal and about 25 wt. % methacrolein. Another preferred mixture of aldehydes has a composition ranging between about 30 wt. % isobutanal and about 70 wt. % methacrolein to about 70 wt. % isobutanal and about 30 wt. % methacrolein. Another preferred mixture of aldehydes has a composition ranging between about 35 wt. % isobutanal and about 65 wt. % methacrolein to about 65 wt. % isobutanal and about 35 wt. % methacrolein. Another preferred mixture of aldehydes has a composition ranging between about 40 wt. % isobutanal and about 60 wt. % methacrolein to about 60 wt. % isobutanal and about 40 wt. % methacrolein. Another preferred mixture of aldehydes has a composition ranging between about 45 wt. % isobutanal and about 55 wt. % methacrolein to about 55 wt. % isobutanal and about 45 wt. % methacrolein. Another preferred mixture of aldehydes has a composition between about 50 wt. % isobutanal and about 50 wt. % methacrolein.

The preferred aldehyde feedstock ranges are designed to cover all feed stock compositions that an operator of such a combined facility may encounter during plant operation. The integrated facility is designed to handle any aldehyde compositional range depending on the availability of each aldehyde during plant operations. Thus, if the methacrolein production reactor is working at a higher output than the butanals production reactor, then the aldehyde feedstock will include more methacrolein than isobutanal and if the butanals production reactor is working at a higher output that the methacrolein production reactor, then the aldehyde feedstock will include more isobutanal than methacrolein.

The integrated facility also makes production of methacrylate polymer and copolymers more efficient because the monomer will not have to be transported from distant facilities. The only feedstock not produced by the facility is methanol if it is needed to make methyl-methacrylate. The facility is ideally suited for preparing butyl-methacrylate and 2-ethyl-hexyl-methacrylates polymers and copolymers directly without the problem of having to transport either the alcohol or the methacrylic acid to an offsite facility.

The present invention has as some of its goals to provide a system and method for producing methacrylic acid and 2-ethyl-hexanol and its derivatives in a more efficient manner, providing better use of by-product or undesired products and providing improved design flexibility. As is set forth below, not all catalysts that oxidize isobutanal or methacrolein are capable of converting mixtures of isobutanal and methacrolein to methacrylic acid. Another aspect of the system and apparatus of this invention is that the catalyst used in the oxidation of a mixture of isobutanal and methacrolein must be capable of converting substantially all isobutanal regardless of its conversion efficiency of methacrolein, as the odor index for isobutanal is very low, i.e., even small concentrations of isobutanal will result in an unpleasant odor in the final methacrylic acid product. One advantage of the systems and methods of this invention involves providing a route to convert isobutanal, generally a 2-ethyl-hexanol plant waste, into a high value product such as methacrylic acid. Because a high value use of isobutanal is provided, the 2-ethyl-hexanol plant can use lower cost catalysts allowing greater design flexibility because any increased isobutanal production is simply used to increase methacrylic acid production or to lower usage of the methacrolein precursor at the same production of methacrylic acid. In addition, the systems and apparatuses of this invention allow increased flexibility to operators of the 2-ethyl-hexanol plants because the operator can adjust the conditions and the catalyst in the hydroformylation reactor to increase overall yield and to decrease production costs even if doing so results in increased isobutanal production. This increased flexibility is due to the fact that isobutanal is no longer an unwanted waste, but can now be used as a valuable feedstock for methacrylic acid production. The systems and apparatuses of this invention also allow the operator of a combined plant to adjust production of methacrylic acid, 2-ethyl-hexanol, n-butanal, and their corresponding esters, monomers, polymers, and copolymers, according to changes in demand and price. The experiments described below evidence preferred catalysts that are capable of not only efficiently oxidizing isobutanal-methacrolein mixtures, but are capable of substantially quantitatively converting isobutanal to methacrylic acid.

EXPERIMENTAL SECTION

General Catalytic Considerations

The following examples illustrate the preparation, calcination and testing of specific catalytic formulations of this invention and of comparative catalysts. Example 1 illustrates the preparation of a specific catalyst of this invention including both B and Bi, while Comparative Example 1 illustrates the preparation of a catalyst excluding B and Bi. Comparative Examples 2 and 3 are heteropoly acids used to compare the catalysts of this invention for the conversion of isobutanal, methacrolein and mixtures thereof. Examples are also included that analyze the performance data for the catalysts of this invention and the comparative examples. Although the conversion of aldehyde feedstock comprising one hundred percent of either isobutanal or methacrolein is not contemplated for use in the facilities of this invention, the following examples illustrate the activities and selectivities of a preferred catalyst of this invention in making methacrylic acid from the pure aldehydes and a 50:50 mixture of the two aldehydes.

Catalysts Preparations

Example 1

The following example illustrates the preparation of a 50 g batch of a catalyst of this invention having the following formula $Mo_{12}P_{1.5}V_{0.5}Cu_{0.1}Bi_{0.5}Sb_{0.8}Cs_{1.0}B_{0.5}O_g$.

46.49 g of ammonium paramolybdate were added to 200 mL of de-ionized (DI) water at room temperature. 1.28 g of ammonium metavanadate were added to the above solution with mixing at room temperature. The mixture was stirred at room temperature until all particles were dissolved to produce an MoV solution. 4.28 g of cesium nitrate were then added to 25 mL of DI water, and the resulting solution was added to the MoV solution with mixing to form an MoVCs solution. 3.80 g of phosphoric acid were then dissolved in 6 mL of DI water and the resulting solution was added to the MoVCs solution with mixing to form an MoVCsP solution. 0.51 g of copper nitrate were added to 5 mL of DI water and the resulting solution was added to the MoVCsP solution with mixing to form an MoVCsPCu solution. 11.32 g of nitric acid were added to 30 grams of DI water, then 7 mL of ammonium hydroxide (28 wt. % solution) were added to the nitric acid solution and then 5.32 g of bismuth nitrate were added to the nitric acid/ammonium hydroxide solution with mixing and the mixture was stirred until the bismuth nitrate went into solution to form a Bi solution. The Bi solution was then added to the MoVCsPCu solution with mixing forming an MoVCsPCuBi slurry. The Bi solution causes a precipitation of the components as it is added to the MoVCsPCu solution or as the MoVCsPCu solution is added to the Bi solution. The resulting MoVCsPCuBi slurry was then heated to 95° C. and then 2.56 g of antimony trioxide and 0.68 g of boric acid were added to the MoVCsPCuBi slurry with mixing to form an MoVCsPCuBiSbB slurry.

The MoVCsPCuBiSbB slurry was then evaporated at about 100° C. to form an evaporated mixture. The evaporated mixture was then dried at about 130° C. for about 16 hours and sieved to obtain particles having a size between about 20 and 30 mesh. The particles were then heated to a soak temperature of 230° C. at a rate of 0.5° C./min and held at the soak temperature for 3 hours in air. The particles were then heated to a calcination temperature of 380° C. at a rate of 0.5° C./min.

and held at the calcination temperature for 5 hours in air to form the $Mo_{12}P_{15}V_{0.5}Cu_{0.1}Bi_{0.5}Sb_{0.8}Cs_{1.0}B_{0.5}O_g$ catalyst.

Comparative Example 1

This example illustrates the preparation of a 50 g batch of a catalyst of this invention having the composition $Mo_{12}P_{15}V_{0.5}Cu_{0.1}Sb_{0.8}Cs_{1.0}O_g$.

Ammonium paramolybdate (46.49 g.) were added to 200 mL de-ionized (DI) water at room temperature. Ammonium metavanadate (1.28 g.) were added to above solution. The mixture was stirred at room temperature and all particles were dissolved. Cesium nitrate (4.28 g.) were added to 25 mL DI water, and the solution was added to above mixture. Phosphoric acid (3.80 g.) were dissolved in 6 mL DI water and the solution obtained was added to above mixture. Copper nitrate (0.51 g.) were added to 5 mL DI water and solution obtained was added into the above mixture. Nitric acid (11.32 g.) were added to DI water (30 g.), then 7 mL $NH_4OH$ (28%) were added into this solution, the solution obtained was added to the above mixture. Temperature of the mixture was increased to 95° C. Then, antimony trioxide (2.56 g.) were added to above mixture. The mixture was evaporated at 100° C., dried at 130° C. for 16 hrs, and sieved to obtain 20-30 mesh particles. The particles were then heated to a soak temperature of 230° C. at a rate of 0.5° C./min and held at the soak temperature for 3 hours in air. The particles were then heated to a calcination temperature of 380° C. at a rate of 0.5° C./min. and held at the calcination temperature for 5 hours in air.

Comparative Example 2

This example illustrates the preparation of a catalyst according to Example 1 of U.S. Pat. No. 4,381,411.

40.40 g of $Fe(NO_3)_3$, 13.59 g of $AgNO_3$ and 21.22 g of 85% $H_3PO_4$ were dissolved in 100 mL of water. The resulting solution was evaporated to a dry paste with heating and stirring. Then, after drying and calcining, a catalyst with composition of $Ag_{0.8}FeP_{1.84}O_x$ was obtained.

Comparative Example 3

A sample of the commercially available heteropolyacid catalyst $(NH_4)_3PMoO_{12}$.

Catalyst Performance Data

Test 1

6 cc of the Example 1 catalyst was loaded into a fixed bed reactor and diluted with 9 cc of quartz chips. The catalyst was tested with a vapor stream having the following composition: 4 vol. % isobutryaldehyde (IBA), 30 vol. % steam with the balance being nitrogen and having two different oxygen to IBA mole ratios ($O_2$/HC). By varying reaction temperature and vapor stream flow rate, conversion and selectivity data were obtained under a variety of conditions. The resulting effluent stream was analyzed by gas chromatography (GC).

To understand the following results, the following definitions are set forth:

% IBA conversion=$[(IBA_i-IBA_f)/IBA_i]*100$

% MAA selectivity=$[(MAA)/(IBA_i-IBA_f)]*100$

% MAC selectivity=$[(MAC)/(IBA_i-IBA_f)]*100$.

To determine the amount of IBA left in the product, products after the reaction are trapped in a Dewar flask at 0° C. Analysis of the liquid collected did not show any trace of IBA. Based on the accuracy of a GC flame ionization detector (FID detector), the conversion of IBA is at least higher than about 99.95%.

The catalytic results are shown in Table I.

TABLE I

IBA Conversion Performance of the Catalyst of Example 1

| Flow Rate (sccm) | T (° C.) | $O_2$/HC | IBA Conversion (%) | MAC Selectivity (%) | MAA Selectivity (%) | Total Selectivity (%) |
|---|---|---|---|---|---|---|
| 100 | 280 | 2.0 | 100 | 30.4 | 53.4 | 83.8 |
| 75 | 281 | 2.0 | 100 | 15.5 | 65.1 | 80.6 |
| 64 | 282 | 2.0 | 100 | 13.6 | 62.9 | 76.5 |
| 57 | 282 | 2.0 | 100 | 7.5 | 67.9 | 75.4 |
| 50 | 281 | 2.0 | 100 | 5.9 | 66.7 | 72.6 |
| 100 | 283 | 2.4 | 100 | 28.7 | 54.4 | 83.1 |
| 75 | 282 | 2.4 | 100 | 15.9 | 63.2 | 79.1 |
| 64 | 282 | 2.4 | 100 | 12.6 | 64.5 | 77.1 |
| 57 | 282 | 2.4 | 100 | 7.8 | 66.9 | 74.7 |
| 50 | 282 | 2.4 | 100 | 5.6 | 67.7 | 73.3 |

Total isobutyraldehyde conversion and around 80% combined methacrolein and methacrylic acid selectivity is obtained with the catalyst of Example 1. Changes in a mole ratio ($O_2$:HC) of oxygen ($O_2$) to hydrocarbon (HC) has little effect on reaction results. Thus, this catalyst is capable of efficiently converting isobutanal to methacrylic acid.

Test 2

6 cc of the Example 1 catalyst was loaded into a fixed bed reactor and diluted with 9 cc of quartz chips. The catalyst was tested with a vapor stream having the following composition: 4 vol. % methacrolein (MAC), 30 vol. % steam with the balance being nitrogen and having two different oxygen to MAC mole ratios ($O_2$/HC) at three different flow rates. The resulting effluent stream was analyzed by gas chromatography (GC).

To understand the following results, the following definitions are set forth:

% MAC conversion=$[(MAC_i-MAC_f)/MAC_i]*100$

% MAA selectivity=$[(MAA)/(MAC_i-MAC_f)]*100$

The catalytic results are shown in Table II.

TABLE II

MAC Conversion Performance of the Catalyst of Example 1

| Flow Rate (sccm) | T (° C.) | $O_2$/HC | MAC Conversion (%) | MAA Selectivity (%) |
|---|---|---|---|---|
| 100 | 278 | 2.0 | 78.4 | 85.2 |
| 75 | 279 | 2.0 | 87.4 | 82.0 |
| 64 | 278 | 2.0 | 94.0 | 80.5 |

The error in the conversion data is about ±3%.

The data indicate that under the same reaction conditions (reaction temperature and oxygen/hydrocarbon mole ratio), this preferred catalyst can also be used to oxidize methacrolein to methacrylic acid.

Test 3

6 cc of the catalysts of Example 1 and Comparative Example 1 were loaded in a fixed bed reactor and diluted with 9 cc of quartz chips. Each catalyst was tested using a feed including 4 vol. % IBA and 30 vol. % steam with the balance being nitrogen in the presence of oxygen at an oxygen to IBA ratio of 2. The products were analyzed by GC. Because IBA is converted to MAA in a two step process going through MAC, the IBA conversion data includes a MAC conversion component as shown in Table III.

To determine the concentration of IBA left in the products, the products after the reaction are trapped in a Dewar at 0° C. Analysis of the liquid collected did not show any trace of isobutanal. Based on the accuracy of GC detector (FID), the conversion of isobutanal is at least higher than 99.95%.

To understand the following results, the following definitions are set forth:

% MAC conversion=[(MAC$_i$+IBA$_i$−MAC$_f$−IBA$_f$)/(MAC$_i$+IBA$_i$)]*100

% MAA selectivity=[(MAA)/(MAC$_i$−MAC$_f$)+(MAA)/(IBA$_i$−IBA$_f$)]*100

The catalyst activities and selectivities for catalysts of Example 1 and Comparative Example 1 obtained under the same reaction temperature (281° C.) are tabulated in TABLE III:

TABLE III

Comparison between Example 1 and Comparative Example 1

| Catalyst | Flow rate (sccm) | IBA conversion (%) | MAC conversion (%) | MAA selectivity (%) |
|---|---|---|---|---|
| Example 1 | 100 | 100 | 74.7 | 83.6 |
|  | 75 | 100 | 84.3 | 78.6 |
|  | 50 | 100 | 94.0 | 71.7 |
| Comparative Example 1 | 100 | 100 | 48.4 | 82.6 |
|  | 75 | 100 | 69.9 | 78.2 |
|  | 50 | 100 | 74.7 | 75.3 |

It can be seen that at the same reaction condition, the catalyst of Example 1 showed higher conversion of methacrolein than the catalyst of Comparative Example 1, and at the same reaction conversion, the catalyst of Example 1 had higher selectivity than the catalyst of Comparative Example 1. Thus, for isobutryaldehyde oxidation, the data clearly indicate that catalysts including Bi and B show better performance than catalyst without Bi and B.

Test 4

6 cc of each of the catalysts of Example 1 and Comparative Examples 2 and 3 were loaded in a fixed bed reactor and diluted with 9 cc of quartz chips. Each catalyst was tested with a feed of 2 vol. % IBA, 2 vol. % of MAC, 30 vol. % steam with the balance being nitrogen in the presence of oxygen at an oxygen to hydrocarbon ratio of 2. The oxidation reactions were carried out at a reaction temperature of 284° C. and at a feed flow rate of 50 sccm. The products were analyzed by GC.

To determine the isobutanal left in the products, products after the reaction are trapped in a Dewar at 0° C. Analysis of the liquid collected did not show any trace of isobutanal. Based on the accuracy of GC detector (FID), the conversion of isobutanal is at least higher than 99.95%.

The reaction results obtained using the catalysts of Example 1, Comparative Example 2 and Comparative Example 3 to convert a 50-50 mixture of IBA and MAC to MAA are tabulated in Table IV.

TABLE IV

Conversion and Selectivity Data for Using IBA/MAC Mixed Feeds

| Catalyst | IBA Conversion (%) | MAC Conversion (%)[a] | Selectivity (%) | One pass yield (%) |
|---|---|---|---|---|
| Example 1 | 100.0 | 93.0 | 83.1 | 77.3 |
| Comp. Example 2 | 100.0 | <30 | <30 | <10 |
| Comp. Example 3 | 100.0 | <20 | <20 | <5 |

[a]MAC Conversion is defined analogously to the definition of IBA Conversion

This data clearly indicated that this preferred catalyst of this invention were capable of simultaneously converting a 50:50 mixtures of IBA and MAC to MAA, while the comparative catalysts showed much lower performance. Looking at the performance data shown in Table IV, it is clear that to achieve several of the goals and advantages of an integrated 2-ethyl-hexanol and methacrylic acid facility, catalyst selection is an important consideration and not any catalyst that is capable of isobutanal oxidation or methacrolein oxidation will work. Again, preferred catalysts are heteropolyacid catalysts that contain at least Mo, P, and V and optional amount of Cu, Bi, B and the second components selected from the group consisting of potassium (K), rubidium (Rb), cesium (Cs), thallium (Tl), and mixtures or combinations thereof, and third components selected from the group consisting of antimony (Sb), cerium (Ce), niobium (Nb), indium (In), iron (Fe), chromium (Cr), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A facility comprising:
   a butanal production and utilization facility adapted to produce n-butanal and products derived therefrom and iso-butanal as a by-product, and
   a methacrylic acid production and utilization facility including:
      a first reactor adapted to convert a methacrolein precursor into methacrolein, to produce a methacrolein-containing stream;
      a separate iso-butanal by-product-containing stream comprising the iso-butanal by-product, and
      a second reactor having an input configured to receive the methacrolein-containing stream and the iso-butanal by-product-containing stream, wherein the second reactor is further adapted to simultaneously convert a mixture of methacrolein and iso-butanal into methacrylic acid with substantially quantitative conversion of the iso-butanal,
   where the second reactor uses a heteropolyacid catalyst capable of simultaneously oxidizing a mixture comprising methacrolein and iso-butanal to methacrylic acid with substantially quantitative conversion of the isobutanal, where the heteropolyacid catalyst comprises at least Mo, P, V, Bi, B, and Cu, where the butanal production and utilization facility and the methacrylic acid production and utilization facility form an integrated facility.

2. The facility of claim 1, wherein the butanal production and utilization facility comprises:
   a hydroformylation reactor adapted to convert propene and syn gas into a butanals product comprising n-butanal and iso-butanal,
   a separation unit adapted to separate the butanals product into an n-butanal product and an iso-butanal product.

3. The facility of claim 2, wherein the butanal production and utilization facility further comprises:
   a 2-ethyl hexanol unit adapted to convert a first portion of the n-butanal product into a 2-ethyl hexanol product,
   an n-butanal polymerization unit adapted to convert a second portion of the n-butanal product into a polymer product, where the polymers comprise n-butanal derived monomer units, and
   an n-butanol unit adapted to convert a third portion of the n-butanal product into an n-butanol product.

4. The facility of claim 1, wherein the methacrylic acid production and utilization facility comprises:
   a methacrolein production unit designed to convert a methacrolein precursor into a methacrolein product in the presence of oxygen and a first oxidation catalyst, and
   a methacrylic acid production unit designed to convert the methacrolein product and the iso-butanal product in the presence of oxygen and the heteropolyacid catalyst into a methacrylic acid product.

5. The facility of claim 4, wherein the methacrylic acid production and utilization facility further comprises:
   a methyl-methacrylate production unit adapted to convert a first portion of the methacrylic acid product and methanol in the presence of an esterification catalyst into a methyl-methacrylate product.

6. The facility of claim 1, wherein the input for the second reactor is configured to receive the methacrolein-containing stream and the isobutanal-by-product-containing stream separately.

7. The facility of claim 1, wherein the input for the second reactor is configured to receive the methacrolein-containing stream and the isobutanal-by-product-containing stream combined.

8. A system comprising:
   a butanal production and utilization facility including:
      a butanals production reactor having:
         a propylene inlet connected to a source of propylene,
         a syn gas inlet connected to a source of syn gas,
         a hydroformylation catalyst, and
         a butanals reactor outlet,
         where the butanals reactor is adapted to convert propylene and syn gas into a mixture of n-butanal and isobutanal,
      a butanals separator having:
         a butanals inlet connected to the butanals reactor output,
         an n-butanal separator outlet, and
         an isobutanal separator outlet,
         here the separator is adapted to separate n-butanal from isobutanal and to produce a separate isobutanal by-product-containing steam comprising the isobutanal, and
   a methacrylic acid production and utilization facility including:
      a first methacrolein production reactor having:
         a methacrolein precursor inlet connected to a source of methacrolein precursor,
         a first oxidizing agent inlet connected to a first source of a first oxidizing agent,
         a mixed metal oxide catalyst,
         a methacrolein outlet,
         where the methacrolein production reactor is adapted to convert the methacrolein precursor into a methacrolein-containing stream comprising methacrolein; and
      a second methacrylic acid production reactor having:
         an inlet configured to receive the methacrolein-containing stream and the isobutanal by-product-containing stream,
         a second oxidizing agent inlet connected to a second source of a second oxidizing agent,
         a heteropolyacid catalyst capable of simultaneously oxidizing a mixture comprising methacrolein and iso-butanal to methacrylic acid with substantially quantitative conversion of the iso-butanal, where the heteropolyacid catalyst comprises at least Mo, P, V, Bi, B, and Cu, and
         a methacrylic acid outlet,
         where the second methacrylic acid production reactor is adapted to simultaneously convert the methacrolein and isobutanal into methacrylic acid with substantially quantitative conversion of the iso-butanal,
   where the butanal production and utilization facility and the methacrylic acid production and utilization facility form an integrated facility.

9. The system of claim 8, wherein the butanal production and utilization facility further includes:
   a butanol production component having:
      an n-butanal inlet connected to the n-butanal separator outlet,
      a hydrogen inlet connected to a source of hydrogen,
      a hydrogenation catalyst,
      where the butanol production component converts n-butanal into n-butanol.

10. The system of claim 8, wherein the butanal production and utilization facility further includes:
    a 2-ethyl-hexanol production component having:
       an n-butanal inlet connected to the n-butanal separator outlet,
       a dimerization catalyst,
       a hydrogen inlet connected to a source of hydrogen, and
       a hydrogenation catalyst,
       where the 2-ethyl-hexanol production component converts n-butanal into 2-ethyl-hexanol.

11. The system of claim 8, wherein the butanal production and utilization facility further includes:
    an n-butanal polymerization unit having:
       an n-butanal inlet;
       an optional co-monomer inlet,
       a polymer product outlet,
       where the polymerization unit is adapted to convert n-butanal and the optional co-monomer in the presence of a polymerization catalyst into polymers including n-butanal derived monomer units.

12. The system of claim 8, wherein the methacrylic acid production and utilization facility further includes:
    a methyl-methacrylate production unit having:
       a methacrylic acid inlet,
       a methanol inlet,
       a methyl-methacrylate outlet,
       where the methyl-methacrylate production unit is adapted to convert the methacrylic acid and the methanol in the presence of an esterification catalyst into a methyl-methacrylate product.

13. The system of claim 9, wherein the methacrylic acid production and utilization facility further includes:
a butyl-methacrylate production unit having:
a methacrylic acid inlet,
an-butanol inlet connected to then-butanol outlet,
a butyl-methacrylate outlet,
where the butyl-methacrylate production unit is adapted to convert the methacrylic acid and then-butanol in the presence of an esterification catalyst into a butyl-methacrylate product.

14. The system of claim 10, wherein the methacrylic acid production and utilization facility further includes:
a 2-ethyl-hexyl-methacrylate production unit having:
a methacrylic acid inlet,
a 2-ethyl-hexanol inlet connected to the 2-ethyl-hexanol outlet, a 2-ethyl-hexyl-methacrylate outlet,
where the 2-ethyl-hexyl-methacrylate production unit is adapted to convert the methacrylic acid and the 2-ethyl-hexanol in the presence of an esterification catalyst into a 2-ethyl-hexyl-methacrylate product.

15. The system of claim 8, wherein the methacrylic acid production and utilization facility further includes:
a polymerization unit having:
a methacrylic acid inlet,
an optional co-monomer inlet,
a polymer outlet,
where the polymerization unit is adapted to convert methacrylic acid and the optional co-monomer into polymers comprising methacrylic acid derived monomer units.

16. The system of claim 12, wherein the methacrylic acid production and utilization facility further includes:
a polymerization unit having:
a methyl-methacrylate inlet,
an optional co-monomer inlet,
a polymer outlet,
where the polymerization unit is adapted to convert methyl-methacrylate and the optional co-monomer into polymers comprising methyl-methacrylate derived monomer units.

17. The system of claim 13, wherein the methacrylic acid production and utilization facility further includes:
a polymerization unit having:
a butyl-methacrylate inlet,
an optional co-monomer inlet,
a polymer outlet,
where the polymerization unit is adapted to convert methyl-methacrylate and the optional co-monomer into polymers comprising butyl-methacrylate derived monomer units.

18. The system of claim 14, wherein the methacrylic acid production and utilization facility further includes:
a polymerization unit having:
a 2-ethyl-hexyl-methacrylate inlet,
an optional co-monomer inlet,
a polymer outlet,
where the polymerization unit is adapted to convert methyl-methacrylate and the optional co-monomer into polymers comprising 2-ethyl-hexyl-methacrylate derived monomer units.

19. The system of claim 8, wherein the methacrylic acid production reactor further includes:
a methacrolein inlet connected to the methacrolein outlet; and
an isobutanal inlet connected to the isobutanal separator outlet.

20. The system of claim 8, wherein the heteropolyacid catalyst in the second reactor further comprises an element selected from the group consisting of potassium (K), rubidium (Rb), cesium (Cs), thallium (Tl), and mixtures or combinations thereof.

21. The system of claim 8, wherein the heteropolyacid catalyst in the second reactor further comprises an element selected from the group consisting of antimony (Sb), cerium (Ce), niobium (Nb), indium (In), iron (Fe), chromium (Cr), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof.

22. The system of claim 8, wherein the heteropolyacid catalyst in the second reactor further comprises Bi and/or B and Cu and an element selected from the group consisting of potassium (K), rubidium (Rb), cesium (Cs), thallium (Tl), and mixtures or combinations thereof.

23. The system of claim 8, wherein the heteropolyacid catalyst in the second reactor further comprises Bi and/or B and Cu and an element selected from the group consisting of antimony (Sb), cerium (Ce), niobium (Nb), indium (In), iron (Fe), chromium (Cr), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof.

24. The system of claim 8, wherein the heteropolyacid catalyst in the second reactor further comprises Bi and/or B and Cu and a first element selected from the group consisting of potassium (K), rubidium (Rb), cesium (Cs), thallium (Tl), and mixtures or combinations thereof and a second element selected from the group consisting of antimony (Sb), cerium (Ce), niobium (Nb), indium (In), iron (Fe), chromium (Cr), arsenic (As), silver (Ag), zinc (Zn), germanium (Ge), gallium (Ga), zirconium (Zr), magnesium (Mg), barium (Ba), lead (Pb), tin (Sn), titanium (Ti), aluminum (Al), silicon (Si), tantalum (Ta), tungsten (W), lanthanum (La), and mixtures or combinations thereof.

25. The system of claim 8, wherein the input for the second methacrylic acid production reactor is configured to receive the methacrolein-containing stream and the isobutanal-by-product-containing stream separately.

26. The system of claim 8, wherein the input for the second methacrylic acid production reactor is configured to receive the methacrolein-containing stream and the isobutanal-by-product-containing stream combined.

* * * * *